US011957765B2

(12) United States Patent
Passini et al.

(10) Patent No.: US 11,957,765 B2
(45) Date of Patent: Apr. 16, 2024

(54) GENE THERAPY FOR NEUROMETABOLIC DISORDERS

(71) Applicant: Genzyme Corporation, Cambridge, MA (US)

(72) Inventors: Marco A. Passini, Shrewsbury, MA (US); James Dodge, Worcester, MA (US)

(73) Assignee: Genzyme Corporation, Cambridge, MA (US)

( * ) Notice: Subject to any disclaimer, the term of this patent is extended or adjusted under 35 U.S.C. 154(b) by 766 days.

(21) Appl. No.: 16/808,206

(22) Filed: Mar. 3, 2020

(65) Prior Publication Data

US 2020/0306387 A1 Oct. 1, 2020

Related U.S. Application Data

(60) Division of application No. 11/934,325, filed on Nov. 2, 2007, now Pat. No. 10,632,213, which is a continuation of application No. PCT/US2006/017242, filed on May 2, 2006.

(60) Provisional application No. 60/685,808, filed on May 31, 2005, provisional application No. 60/677,057, filed on May 2, 2005.

(51) Int. Cl.
| | |
|---|---|
| *A61K 48/00* | (2006.01) |
| *C07K 14/47* | (2006.01) |
| *C12N 15/86* | (2006.01) |
| *C12N 15/864* | (2006.01) |

(52) U.S. Cl.
CPC .......... *A61K 48/0075* (2013.01); *A61K 48/00* (2013.01); *C07K 14/47* (2013.01); *C12N 15/86* (2013.01); *C12N 15/8645* (2013.01); *C12N 2750/14041* (2013.01); *C12N 2750/14143* (2013.01); *C12N 2799/025* (2013.01)

(58) Field of Classification Search
CPC .... A61K 48/0075; A61K 48/00; C07K 14/47; C12N 15/86; C12N 15/8645; C12N 2750/14041; C12N 2750/14143; C12N 2799/025
USPC ...................... 514/44 R; 435/320.1, 456, 212
See application file for complete search history.

(56) References Cited

U.S. PATENT DOCUMENTS

| | | | |
|---|---|---|---|
| 5,658,776 A | 8/1997 | Flotte et al. | |
| 5,672,344 A | 9/1997 | Kelley et al. | |
| 5,773,278 A | 6/1998 | Schuchman et al. | |
| 6,042,576 A | 3/2000 | DeVries | |
| 6,180,613 B1 | 1/2001 | Kaplitt et al. | |
| 6,503,888 B1 | 1/2003 | Kaplitt et al. | |
| 6,541,218 B1 | 4/2003 | Schuchman et al. | |
| 6,544,785 B1 | 4/2003 | Palese et al. | |
| 6,667,174 B2 | 12/2003 | Yew | |
| 10,632,213 B2 | 4/2020 | Passini et al. | |
| 10,744,210 B2 | 8/2020 | Dodge et al. | |
| 2003/0118552 A1 | 6/2003 | Kasper et al. | |
| 2003/0118556 A1 | 6/2003 | Kasper et al. | |
| 2003/0165481 A1 | 9/2003 | Hersh | |
| 2003/0228282 A1 | 12/2003 | Gao et al. | |
| 2004/0258666 A1* | 12/2004 | Passini ................. | A61K 38/465 514/44 R |
| 2007/0275449 A1 | 11/2007 | Wu et al. | |
| 2008/0029593 A1 | 11/2008 | Passini et al. | |
| 2009/0069261 A1 | 3/2009 | Dodge et al. | |
| 2009/0117156 A1 | 5/2009 | Passini et al. | |
| 2014/0356327 A9 | 12/2014 | Passini et al. | |
| 2015/0030561 A1 | 1/2015 | Dale et al. | |
| 2021/0008074 A1 | 1/2021 | Joseph et al. | |

FOREIGN PATENT DOCUMENTS

| | | |
|---|---|---|
| CN | 1575340 A1 | 2/2005 |
| EP | 0130166 A1 | 2/1985 |
| EP | 1879625 B1 | 12/2010 |
| WO | WO-1995/00655 A1 | 1/1995 |
| WO | WO-1995/011984 A3 | 5/1995 |
| WO | WO-1995/027071 A3 | 10/1995 |
| WO | WO-1995/027071 A9 | 10/1995 |
| WO | WO-2001/036603 A2 | 5/2001 |
| WO | WO-2003/055983 A2 | 7/2003 |
| WO | WO-2004/098648 A1 | 11/2004 |
| WO | 2005035743 A1 | 4/2005 |

OTHER PUBLICATIONS

Burger et al. (2004) Mol. Ther., vol. 10, 302-317.*
Auricchio, A. et al. (Dec. 15, 2001). "Exchange of Surface Proteins Impacts on Viral Vector Cellular Specificity and Transduction Characteristics: The Retina as a Model," *Hum. Mol. Genet.* 10(26):3075-3081.
Ausubel, F.M. et al. (1987). *Current Procedure in Molecuarl Biology*, John Wiley & Sons, New York, New York, seven pages, (Table of Contents Only.).
Azzouz, M. et al. (May 27, 2004). "VEGF Delivery With Retrogradely Transported Lentivector Prolongs Survival In a Mouse ALS Model," *Nature* 429:413-417.
Bartlett, J.S. et al. (May 20, 1998) "Selective and Rapid Uptake of Adeno-Associated Virus Type 2 in Brain," *Hum. Gene Ther.* 9:1181-1186.
Boillée, S. et al. (Jan. 2004). "Gene Therapy for ALS Delivers," *Trends in Neuroscience* 27(5):235-238.

(Continued)

*Primary Examiner* — Anne Marie S Wehbe
(74) *Attorney, Agent, or Firm* — MORRISON & FOERSTER LLP

(57) ABSTRACT

The disclosure pertains to methods and compositions for treating disorders affecting the central nervous system (CNS). These disorders include neurometabolic disorders such as lysosomal storage diseases that affect the central nervous system, e.g., Niemann-Pick A disease. They also include disorders such as Alzheimer's disease. The disclosed methods involve contacting an axonal ending of a neuron with a composition containing high titer AAV carrying a therapeutic transgene so that the AAV vector is axonally transported in a retrograde fashion and transgene product is expressed distally to the administration site.

9 Claims, 18 Drawing Sheets

(56) References Cited

OTHER PUBLICATIONS

Bosch, A. et al. (Jan. 2000). "Long-Term and Significant Correction of Brain Lesion s in Adult Mucopolysaccharidosis Type VII Mice Using Recombinant AAV Vectors," *Molecular Therapy* 1(1):63-70. (From the client).

Breakefield, X.O. et al. (Mar. 1991). "Herpes Simplex Virus for Gene Delivery to Neurons," *New Biol.* 3(3):203-218.

Bruijn, L.I. et al. (2004). "Unraveling the Mechanisms Involved in Motor Neuron Degeneration in ALS," *Annu. Rev. Neurosci.* 27:723-749.

Burger, C. et al. (Aug. 2004, e-pub. Jul. 1, 2004). "Recombinant AAV Viral Vectors Pseudotyped with Viral Capsids from Serotypes 1, 2, and 5 Display Differential Efficiency and Cell Tropism After Delivery to Different Regions of the Cental Nervous System," *Mol. Ther.* 10(2):302-317.

Carpenter, S. (Sep. 1968). "Proximal Axonal Enlargement in Motor Neuron Disease," *Neurology* 18:841-851.

Chamberlin, N.L. et al. (May 18, 1998). "Recombinant Adeno-Associated Virus Vector: Use for Transgene Expression and Anterograde Tract Tracing in the CNS," *Brain Res.* 793:169-175.

Clark, K.R. et al. (Apr. 10, 1999). "Highly Purified Recombinant Adeno-Associated Virus Vectors are Biologically Active and Free of Detectable Helper and Wild-type Viruses," *Hum. Gene Ther.* 10:1031-1039.

Clement, A.M. et al. (Oct. 3, 2003). "Wild-Type Nonneuronal Cells Extend Survival of SOD1 Mutant Motor Neurons in ALS Mice," *Science* 302:113-117, erratum Oct. 24, 2003, 1 page.

Cleveland, D.W. et al. (Nov. 2001). "From Charcot to Lou Gehrig: Deciphering Selective Motor Neuron Death in ALS," *Nat. Rev. Neurosci.* 2(11):806-819.

Datto, J. et al. (Nov. 2002). "Distribution of AAV-1 GFP With Respect to Time, Distance, Traveled and Expression Following Injection to the Midbrain," *Meeting for Society for Neuroscience*, Orlando, Florida, Nov. 3-7, 2002, Abstract No. 623.4, two pages. (From the client).

Davidson, B.L. et al. (May 2003). "Viral Vectors for Gene Delivery to the Nervous System," *Nat. Rev.* 4:353-364.

Defalco, J. et al. (Mar. 30, 2001). "Virus-assisted Mapping of Neural Inputs to a Feeding Center in the Hypothalamus," *Science* 291:2608-2613.

Delisle, M.B. et al. (Feb. 1984). Neurofibrillary Axonal Swellings and Amyotrophic Lateral Sclerosis. *J. Neurol. Sci.* 63(2):241-250.

Ding, W. et al. (2005, e-pub. Apr. 14, 2005). "Intracellular Trafficking of Adeno-Associated Viral Vectors," *Gene Therapy* 12:873-880.

Donello, J.E. et al. (Jun. 1998). "Woodchuck Hepatitis Virus Contains a Tripartite Posttranscriptional Regulatory Element," *Journal of Virology* 72(6):5085-5092.

Doré, S. et al. (Aug. 1997). "Rediscovering an Old Friend, IGF-I: Potential Use in the Treatment of Neurodegenerative Diseases," *Trends Neurosci.* 20(8):326-331.

Duvernoy, H.M. (1999). *The Human Brain. Surface, Three-Dimensional Sectional Anatomy With MRI, and Blood Supply*, SpringerWien, New York, New York, five pages, (Table of Contents).

Elbashir, S.M. et al. (Jan. 15, 2001). "RNA Interference is Mediated by 21- and 22-Nucleotide RNAs," *Genes Dev.* 15(2):188-200.

Extended European Search Report dated Feb. 25, 2009, for European Patent Application No. 06752135.1, filed on May 2, 2006, 5 pages.

Fisher, K.J. et al. (Jan. 1996). "Transduction with Recombinant Adeno-Associated Virus for Gene Therapy is Limited by Leading-strand Synthesis," *J. Virol.* 70:520-532.

Gal, A.E. et al. (Sep. 25, 1975). "A Practical Chromogenic Procedure for the Detection of Homozygotes and Heterozygous Carriers of Niemann-Pick Disease," *N. Engl. J. Med.* 293(13):632-636.

Gao, G.P. et al. (Sep. 3, 2002). "Novel Adeno-Associated Viruses from Rhesus Monkeys as Vectors for Human Gene Therapy," *Proc. Natl. Acad. Sci. U.S.A.* 99(18):11854-11859.

Gonatas, N.K. et al. (Mar. 1992). "Fragmentation of the Golgi Apparatus of Motor Neurons in Amyotrophic Lateral Sclerosis," *Am. J. Pathol.* 140(3):731-737.

Gurney, M.E. et al. (Jun. 17, 1994). "Motor Neuron Degeneration in Mice That Express a Human Cu, Zn Superoxide Dismutase Mutation," *Science* 264:1772-1775.

Haberman, R.P. et al. (1998). "Inducible Long-Term Gene Expression in Brain With Adeno-Associated Virus Gene Transfer," *Gen Ther.* 5:1604-1611.

Harlow, E. et al. eds. (1988). *Antibodies, A Laboratory Manual*, and *Animal Cell Culture*, Freshney, R.I. ed., Cold Spring Harbor Laboratory, pp. iii-ix, (Table of Contents Only.).

Hauck, B. et al. (Feb. 2003). "Characterization of Tissue Tropism Determinants of Adeno-Associated Virus Type 1", *Journal of Virology* 77(4):2768-2774.

Hermonat, P.L. et al. (Oct. 1984). "Use of Adeno-Associated Virus as a Mammalian DNA Cloning Vector: Transduction of Neomycin Resistance Into Mammalian Tissue Culture Cells," *Proc. Natl. Acad. Sci. U.S.A.* 81:6466-6470.

Hirano, A. (Oct. 1996). "Neuropathology of ALS: An Overview," *Neurology* 47(Supp. 2):S63-S66.

Hirano, A. et al. (Sep. 1984). "Fine Structural Study of Neurofibrillary Changes in a Family With Amyotrophic Lateral Sclerosis," *J. Neuropathol. & Exp. Neurol.* 43(5):471-480.

Horinouchi, K. et al. (Jul. 1995). "Acid Sphingomyelinase Deficient Mice: A Model of Types A and B Niemann-Pick Disease," *Nat. Genetics* 10:288-293.

International Search Report dated May 7, 2007, for PCT Application No. PCT/US06/16943, filed on May 2, 2006, four pages.

International Search Report, dated Sep. 15, 2006, for PCT Application No. PCT/US06/17242, filed on May 2, 2006, two pages.

Iwata, N. et al. (Feb. 2000). "Identification of the Major Abeta1-42-Degrading Catabolic Pathway in Brain Parenchyma: Suppression Leads to Biochemical and Pathological Deposition," *Nat. Med.* 6(2):143-150.

Iwata, N. et al. (Jan. 28, 2004). "Presynaptic Localization of Neprilysin Contributes to Efficient Clearance of Amyloid-B Peptide in Mouse Brain," *J. Neurosci.* 24(4):991-998.

Janson, C. et al. (Jul. 20, 2002). "Clinical Protocol. Gene therapy of Canavan Disease: AAV-2 Vector for Neurosurgical Delivery of Aspartoacylase Gene (ASPA) to the Human Brain," *Hum. Gene Ther.* 13:1391-1412.

Jeyakumar, M. et al. (Oct. 2002). "Glycosphingolipid Lysosomal Storage Diseases: Therapy and Pathogenesis," *Neuropath. Appl. Neurobiol.* 28:343-357.

Jin, H.K. et al. (May 2002). "Intracerebral Transplantation of Mesenchymal Stem Cells into Acid Sphingomyelinase-Deficient Mice Delays the Onset of Neurological Abnormalities and Extends Their Life Span," *J. Clin. Invest.* 109:1183-1191.

Kaemmerer, W.F. et al. (2000, e-pub. Oct. 7, 2000). "In Vivo Transduction of Cerebellar Purkinje Cells Using, Adeno-Associated Virus Vectors," *Molecular Therapy* 2(5):446-457.

Kandel, E.R. et al. (1991). *Principles of Neural Science*, Third Edition, McGraw-Hill, New York, New, York, Health Professions Division, pp. ix-xi, (Table of Contents Only).

Kanemitsu, H. et al. (Oct. 23, 2003). "Human Neprilysin is Capable of Degrading Amyloid B Peptide not Only in the Monomeric Form but Also the Pathological Oligomeric Form," *Neurosci. Lett.* 350:113-116.

Kaplitt, M.G. et al. (Oct. 1994). "Long-term Gene Expression and Phenotypic Correction Using Adeno-Associated Virus Vectors in the Mammalian Brain," *Nat. Genet.* 8:148-154.

Kaspar, B.K. et al. (Aug. 8, 2003). "Retrograde Viral Delivery of IGF-1 Prolongs Survival in a Mouse ALS Model," *Science* 301:839-842.

Kaspar, B.K. et al. (Jan. 2002). "Targeted Retrograde Gene Delivery for Neuronal Protection," *Mol. Ther.* 5:50-56.

Klein, R.L. et al. (Apr. 1998). "Neuron-specific Transduction in The rat Septohippocampal or Nigrostriatal Pathway by Recombinant Adeno-Associated Virus Vectors," *Exp. Neurol.* 150:183-194.

(56) References Cited

OTHER PUBLICATIONS

Kurreck, J. (Apr. 2003). "Antisense Technologies. Improvement Through Novel Chemical Modifications," J. Eur. Biochem. 270:1628-1644.
Lebherz, C. et al. (Jun. 2004, e-pub. Mar. 2, 2004). "Gene Therapy with Novel Adeno-Associated Virus Vectors Substantially Diminishes Atherosclerosis in a Murine Model of Familial Hypercholesterolemia," J Gene Med. 6(6):663-672.
Lebkowski, J.S. et al. (Oct. 1988)."Adeno-Associated Virus: A Vector System for Efficient Introduction and Integration of DNA Into a Variety of Mammalian Cell Types," Mol. Cell. Biol. 8(10):3988-3996.
Leigh, P.N. et al. (1991). "Cytoskeletal Pathology in Motor Neuron Diseases," Adv. Neurol. 56:115-124.
Leigh, P.N. et al. (Apr. 1991). "Ubiquitin-Immunoreactive Intraneuronal Inclusions in Amyotrophic Lateral Sclerosis. Morphology, Distribution, and Specificity," Brain 114( Pt 2):775-788.
Leventhal, A.R. et al. (Nov. 30, 2001). "Acid Sphingomyelinase-Deficient Macrophages have Defective Cholesterol Trafficking and Efflux," J. Biol. Chem. 276(48):44976-44983.
Lindsay, R.M. (1994). "Neurotrophic Growth Factors and Neurodegenerative Diseases: Therapeutic Potential of the Neurotrophins and Ciliary Neurotrophic Factor," Neurobiol. Aging 15(2):249-251.
Liu, Y. et al. (2002). "High Level of Transduction of Mammalian Brian by Adeno-Associated Type 1 Virus Vector," Society for Neuroscience, Orlando, Flordia, Nov. 3-7, 2002, Abstract No. 902.2, 2 pages.
Machida, C.A. (2003). Viral Vector for Gene Therapy Methods and Protocols, Springer, Humana Press, pp. vii-x, (Table of Contents Only).
Mai, J.K. et al. (1997). Atlas of the Human Brain, Academic Press, San Diego, CA, pp. vii-viii, (Table of ContentsOnly).
Mandel, R.J. et al. (2000). "Intracerebral Gene Transfer using Viral Vectors," Neuromethods 36:103-130.
Mandel. R.J. et al. (Jun. 1, 1998). "Characterization of Intrastriatal Recombinant Adeno-Associated Virus-Mediated Gene Transfer of Human Tyrosine Hydroxylase and Human GTP-Cyclohydrolase I in a Rat Model of Parkinson's Disease," J. Neurosci. 18(11):4271-4284.
Marr, R.A. et al. (Mar. 15, 2003). "Neprilysin Gene Transfer Reduces Human Amyloid Pathology in Transgenic Mice," J. Neurosci. 23(6):1992-1996.
Marr, R.A et al. (2004). "Neprilysin Regulates Amyloid β Peptide Levels," J. Mol. Neurosci. 22:5-11.
Matsushita, M. (Feb. 1, 1999). "Projections From the Lowest Lumbar and Sacral-Caudal Segments to the Cerebellar Nuclei in the Rat, Studied by Anterograde Axonal Tracing," J. Comp. Neurol. 404(1):21-32.
Matsushita, M. et al. (1990) "Afferents to the Cerebellar Nuclei From the Cervical Enlargement in the Rat, as Demonstrated With the Phaseolus Vulgaris Leucoagglutinin Method," Neurosci. Lett. 113:253-259.
Matsushita, M. et al. (Jan. 13, 1997). "Projections From the Cervical Enlargement to Cerebellar Nuclei in the Rat, Studied by Anterograde Axonal Tracing," J. Comp. Neurol. 377:251-261.
Matsushita, M. et al. (Mar. 1995). "Projections From the Central Cervical Nucleus to the Cerebellar Nuclei in the Rat, Studied by Anterograde Axonal Tracing," J. Comp. Neurol. 353:(2)234-246.
Matsushita, M. et al. (Sep. 29, 1987). "Projections From the Thoracic Cord to the Cerebellar Nuclei in the Rat, Studied by Anterograde Axonal Tracing," J. Comp. Neurol. 386(3):409-421.
McLaughlin, S.K. et al. (Jun. 1988). "Adeno-Associated Virus General Transduction Vectors: Analysis of Proviral Structures," J. Virol. 62(6):1963-1973.
Miranda, S.R. et al. (Oct. 2000). "Hematopoietic Stem Cell Gene Therapy Leads to Marked Visceral Organ Improvements and a Delayed onset of Neurological Abnormalities in the Acid Sphingomyelinase Deficient Mouse Model of Niemann-Pick Disease," Gene Ther. 7:1768-1776.
Miyazaki, J. et al. (Jul. 15, 1989). "Expression Vector System Based on the Chicken Beta-actin Promoter Directs Efficient Production of Interleukin-5," Gene 79:269-277.
Muzyczka, N. (1992). "Use of Adeno-Associated Virus as a General Transduction Vector for Mammalian Cells," Curr. Topics Microb.& Immunol. 158:97-129.
Neufeld, E.F. et al. (Jul. 10, 1970). "Inborn Errors of Mucopolysaccharide Metabolism," Science 169:141-146.
O'Riordan, C.R. et al. (Nov.-Dec. 2000). "Scaleable Chromatographic Purification Process for Recombinant Adeno-Associated Virus (rAAV)," J. Gene Med. 2:444-454.
Otterback, B. et al. (Jun. 30, 1995). "Acid Sphingomyelinase-Deficient Mice Mimic the Neurovisceral Form of Human Lysosomal Storage Disease (Niemann-Pick Disease)," Cell 81:1053-1061.
Pardrigde, (1991). Peptide Drug Delivery to the Brain, Raven Press, Table of Contents, three pages. vii.
Passini, M.A. et al. (2003). "Widespread Gene Delivery and Reversal of Pathology in the Brains of Niemann-Pick a Mice by retrograde Axonal Transport of a Therapeutic AAV Vector," Meeting for the Society for Neuroscience, New Orleans, LA, Nov. 8-12, 2003, 1 page. (Abstract Only).
Passini, M.A. et al. (Aug. 1, 2002). "Distribution of a Lysosomal Enzyme in the Adult Brain by Axonal Transport and by Cells of the Rostral Migratory Stream," J. Neurosci. 22(15):6437-6446.
Passini, M.A. et al. (Jun. 2003). "Intraventricular Brain Injection of Adeno-Associated Virus Type 1 (AAV1) In Neonatal Mice Results In Complementary Patterns of Neuronal Transduction to AAV2 and Total Long-Term Correction of Storage Lesions in The Brains of Beta-Glucuronidase-Deficient Mice," J. Virol. 77(12):7034-7040.
Paxinos, G. (1995). The Rat Nervous System, 2nd ed., Academic Press. San Diego, California, pp. vii-xii, (Table of Contents Only.).
Rabinowitz, J.E. et al. (Jan. 2002). "Cross-Packaging of a Single Adeno-Associated Virus (AAV) Type 2 Vector Genome Into Multiple AAV Serotypes Enables Transduction with Broad Specificity," J. Virol. 76(2):791-801.
Ralph, G.S. et al. (Apr. 2005, e-pub. Mar. 13, 2005). "Silencing Mutant SOD1 Using RNAi Protects Against Neurodegeneration and Extends Survival in an ALS Model," Nat. Med. 11(4):429-433.
Raoul, C. et al. (2005). "Lentiviral-Mediated Silencing of SOD1 Through RNA Interference Retards Disease Onset and Progression in a Mouse Model of ALS," Nat. Med. 11(4):423-438.
Rosen, D.R. et al. (Mar. 4, 1993). "Mutations in Cu/Zn Superoxide Dismutase Gene are Associated With Familial Amyotrophic Lateral Sclerosis," Nature 362(6415):59-62.
Rowland, L.P. et al. (May 31, 2001). Amyotrophic Lateral Sclerosis. N. Engl. J. Med. 344(22):1688-1700.
Sambrook, J. et al. (1989). Molecular cloning: A Laboratory Manual, 2nd Edition, Cold Spring Harbor Laboratory Press, Cold Spring Harbor, New York, pp. v-xxxii, (Table of Contents Only).
Sando, G.N. et al. (Nov. 1977). "Recognition and Receptor-mediated Uptake of a Lysosomal Enzyme, α-L-Iduronidase, by Cultured Human Fibroblasts," Cell 12:619-627.
Sarna, J. et al. (2001). "Patterned Cerebellar Purkinje Cell Death in a Transgenic Mouse Model of Niemann Pick Type A/B Disease," Eur. J. Neurosci. 13:1873-1880.
Schuchman, E.H. et al. (2001). "Niemann-Pick Disease Types A and B: Acid Sphingomyelinase Deficiencies," Chapter 144 in The Metabolic and Molecular Bases of Inherited Diseases, Scriver, C. R. et al., ed., McGraw-Hill, New York, New York, pp. 3589-3610.
Shipley, J.M. et al. (Aug. 1991). "Analysis of the 5' Flanking Region of the Human β-glucuronidase Gene," Genomics 10:1009-1018.
Skorupa, A.F. et al. (Nov. 1999). "Sustained Production of β-Glucuronidase from Localized Sites After AAV Vector Gene Transfer Results in Widespread Distribution of Enzyme and Reversal of Lysosomal Storage Lesions in a Large Volume of Brain in Mucopolysaccharidosis VII Mice," Exp. Neurol. 160:17-27.
Sleat, D.E. et al. (Oct. 13, 2004). "A Mouse Model of Classical Late-Infantile Neuronal Ceroid Lipofuscinosis Based on Targeted Disruption of the CLN2 Gene Results in a Loss of Tripeptidyl-Peptidase I Activity and Progressive Neurodegeneration," J. Neurosci. 24(41):9117-9126.
Slotte, J.P. (1997). "Cholesterol-Sphingomyelin Interactions in Cells—Effects on Lipid Metabolism," Chapter 10 in Subcellular Biochem-

(56) References Cited

OTHER PUBLICATIONS istry, Cholestrol: Its Functions and Metabolism in Biology and Medicine, Bittman, R. ed., Plenum Press, New York, New York, 28:277-293.

Soudias, C. et al. (2001, e-pub. Aug. 17, 2001). "Preferential Transduction of Neurons by Canine Adenovirus Vectors and Their Efficient Retrograde Transport in vivo," FASEB J. 15:2283-2285, 23 pages.

Stewart, G.R. et al. (2002). Behavioral Pathology of the Niemann-Pick A (Asmko) Mouse: Structure-Function Studies on Purkinje Cell Degeneration,: Neuroscience 2002, Orlando, Florida, Poster 503, Development Disorders: Genetic III Poster, one page. (Abstract Only).

Talairach et al. (1988). Co-Planar Stereotaxic Atlas of the Human Brain: 3-Dimensional Proportional System: An Approach to Cerebral Imaging, (Table of Contents.), 2 pages.

Taylor, R.M. et al. (Jul. 1997). "Decreased Lysosomal Storage in the Adult MPS VII Mouse Brain in the Vicinity of Grafts of Retroviral Vector-corrected Fibroblasts Secreting High Levels of β-Glucuronidase," Nat. Med. 3(7):771-774.

The Extended European Search Report dated Jan. 23, 2012, for European Patent Application No. 11169633.2, filed on May 2, 2006, five pages.

Tu, P-H. et al. (Apr. 1996). "Transgenic Mice Carrying a Human Mutant Superoxide Dismutase Transgene Develop Neuronla Cytoskeletal Pathology Resembling Human Amyotrophic Lateral Sclerosis Lesions," Proc. Natl. Acad. Sci. U.S.A. 93:3155-3160.

Veldwijk, M.R. et l. (Aug. 2002). "Development and Optimization of a Real-Time Quantitative PCR-based Method for the Titration of AAV-2 Vector Stocks," Mol. Ther. 6(2):272-278.

Viana, M.B. et al. (Aug. 1990). "Very Low Levels of High Density Lipoprotein Cholesterol in Four Sibs of a Family with Non-neuropathic Niemann-Pick Disease and Sea-blue Histiocytosis," J. Med. Genet. 27:499-504.

Vite, C.H. et al. (2003). "Adeno-Associated Virus Vector-Mediated Transduction in the Cat Brain," Gene Therapy 10:1874-1881.

Walkley, S.U. (1998). "Cellular Pathology of Lysosomal Storage Disorders," Brain Pathol. 8:175-193.

Wang, C. et al. (2003). "Recombinant AAV Serotype 1 Transduction Efficiency and Tropism in the Murine Brain," Gene Therapy 10:1528-1534.

Watson, D.J. et al. (2003). "Lentiviral Vectors for Gene Transfer to the Central Nervous System. Applications in Lysosomal Storage Disease Animal Models," Methods Mol. Med. 76:383-403.

Wu, Z. et al. (Sep. 2006). "α2,3 and α2,6 N-linked sialic acids facilitate efficient binding and transduction by adeno-associated virus types 1 and 6," Journal of Virology 80(18):9093-9103.

Xiao, X. et al. (Mar. 1997). "Gene Transfer by Adeno-Associated Virus Vectors Into the Central Nervous System," Exp. Neurology 144:113-124.

Xu, R. et al. (Sep. 2001). "Quantitative Comparison of Expression with Adeno-Associated Virus (AAV-2) Brain-specific Gene Cassettes," Gene Ther. 8:1323-1332.

Yasojima, K. et al. (Jan. 12, 2001). "Reduced Neprilysin in High Plaque Areas of Alzheimer Brain: A Possible Relationship to Deficient Degradation of β-Amyloid Peptide," Neurosci. Lett. 297:97-100.

Ye, S.J. et al. (Feb. 5, 1995). "Regulating Delivery of Therapeutic Proteins After in Vivo Somatic Cell Gene Transfer," Science 283:88-91.

Yu, J.Y. et al. (Apr. 30, 2002). "RNA Interference by Expression of Short-Interfering RNAs and Hairpin RNAs in Mammalian Cells," Proc. Natl. Acad. Sci. U.S.A. 99(9):6047-6052.

Miranda, S.R.P. et al. (Oct. 2000). "Infusion of Recombinant Human Acid Sphingomyelinase into Niemann-Pick Disease Mice Leads to Visceral, but Not Neurological, Correction of the Pathophysiology", FASEB J. 14:1988-1995.

* cited by examiner

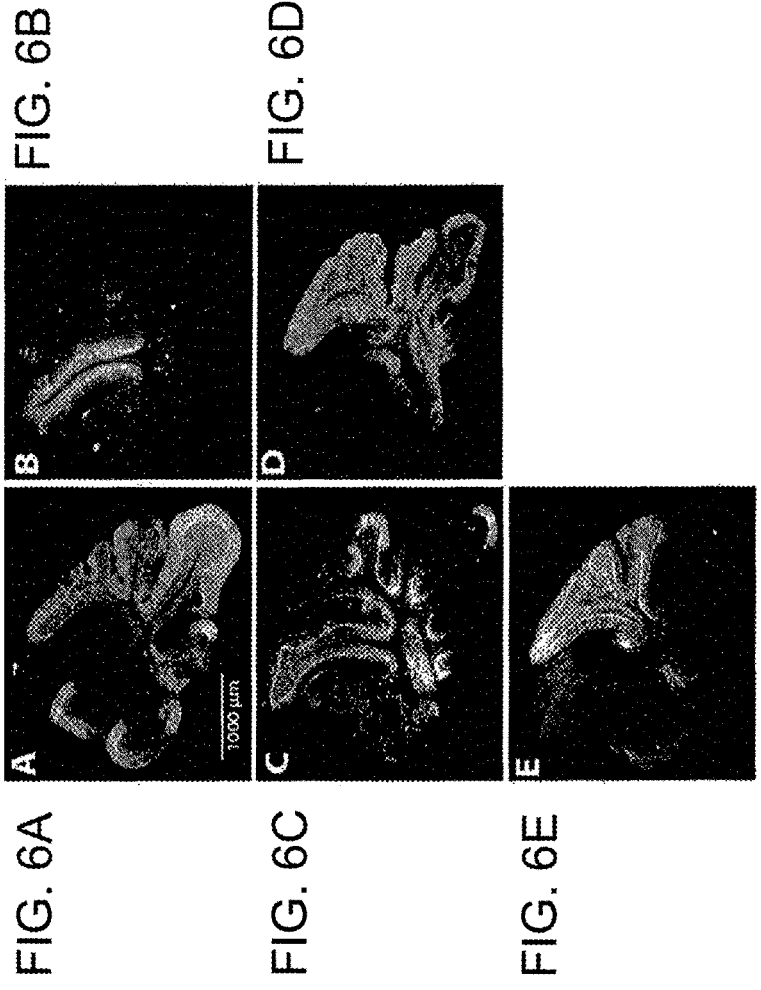

FIG. 9A FIG. 9B FIG. 9C
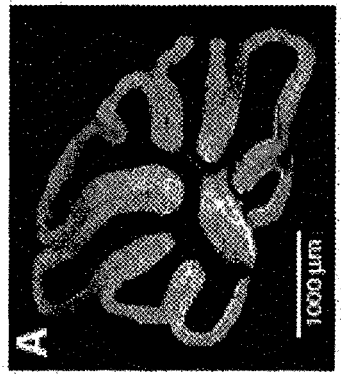
FIG. 9D FIG. 9E FIG. 9F
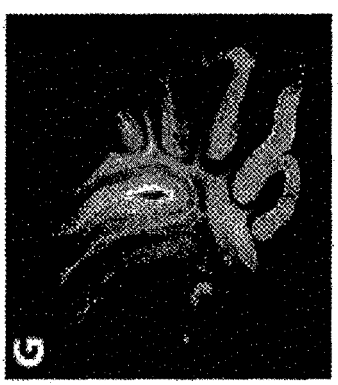
FIG. 9G FIG. 13B
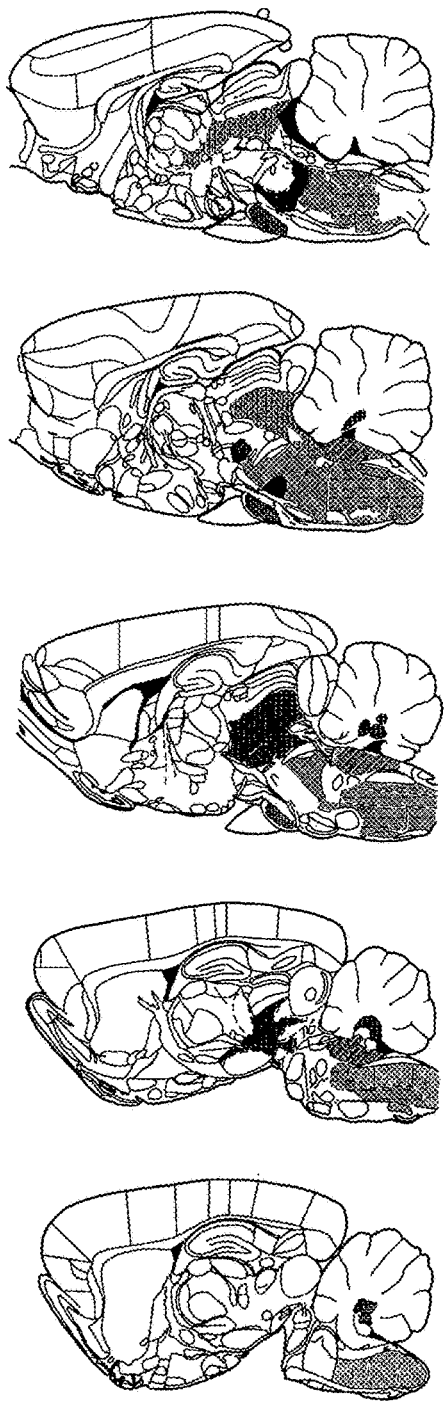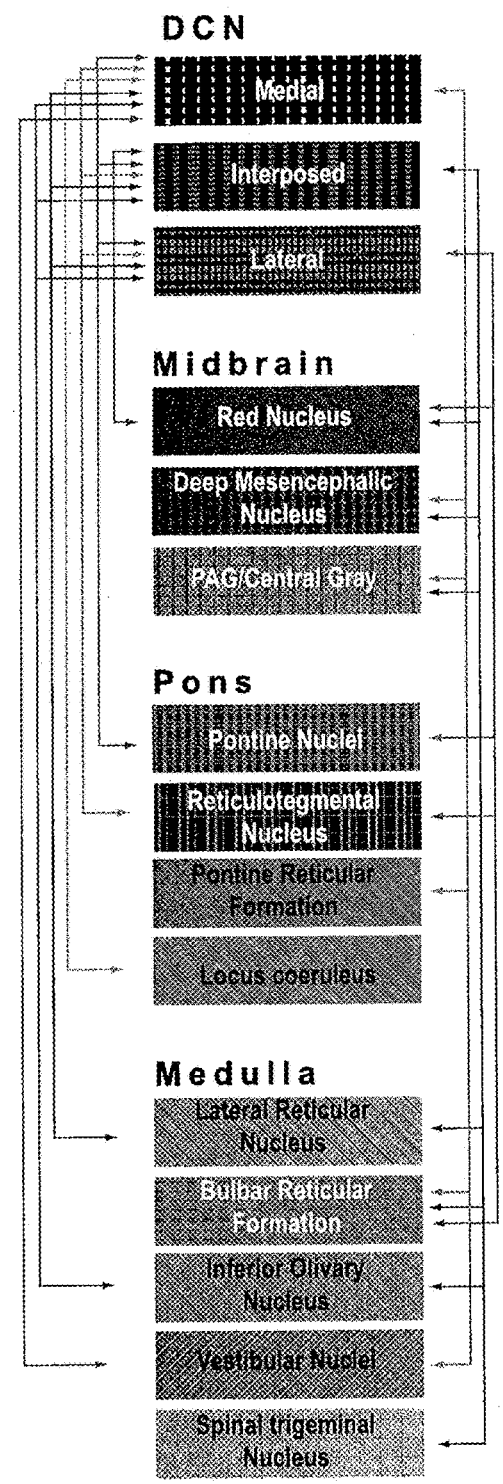

GENE THERAPY FOR NEUROMETABOLIC DISORDERS

CROSS-REFERENCE TO RELATED APPLICATIONS

This application is a divisional application of U.S. patent application Ser. No. 11/934,325, filed Nov. 2, 2007, which is a continuation of PCT/US2006/01 7242, filed May 2, 2006, which claims priority under 35 U.S.C. § 119(e) to U.S. Provisional Application No. 60/677,057, filed May 2, 2005, and U.S. Provisional Application No. 60/685,808, filed May 31, 2005, the contents of which are herein incorporated by reference.

FIELD OF THE INVENTION

The present invention relates to compositions and methods for treating disorders affecting the central nervous system (CNS) and in particular, the spinal cord. The invention further relates to compositions comprising viral vectors such as adeno-associated virus (AAV) vectors, and methods of administration thereof.

BACKGROUND OF THE INVENTION

A group of metabolic disorders known as lysosomal storage diseases (LSD) includes over forty genetic disorders, many of which involve genetic defects in various lysosomal hydrolases. Representative lysosomal storage diseases and the associated defective enzymes are listed in Table 1.

TABLE 1

| Lysosomal storage disease | Defective enzyme |
| --- | --- |
| Aspartylglucosaminuria | Aspartylglucosaminidase |
| Fabry | α-Galactosidase A |
| Infantile Batten Disease* (CNL1) | Palmitoyl Protein Thioesterase |
| Classic Late Infantile Batten Disease* (CNL2) | Tripeptidyl Peptidase |
| Juvenile Batten Disease* (CNL3) | Lysosomal Transmembrane Protein |
| Batten, other forms* (CNL4-CNL8) | Multiple gene products |
| Cystinosis | Cysteine transporter |
| Farber | Acid ceramidase |
| Fucosidosis | Acid α-L-fucosidase |
| Galactosidosialidosis | Protective protein/cathepsin A |
| Gaucher types 1, 2*, and 3* | Acid β-glucosidase, or glucocerebrosidase |
| $G_{M1}$ gangliosidosis* | Acid β-galactosidase |
| Hunter* | Iduronate-2-sulfatase |
| Hurler-Scheie* | α-L-Iduronidase |
| Krabbe* | Galactocerebrosidase |
| α-Mannosidosis* | Acid α-mannosidase |
| β-Mannosidosis* | Acid β-mannosidase |
| Maroteaux-Lamy | Arylsulfatase B |
| Metachromatic leukodystrophy* | Arylsulfatase A |
| Morquio A | N-Acetylgalactosamine-6-sulfate sulfatase |
| Morquio B | Acid β-galactosidase |
| Mucolipidosis II/III* | N-Acetylglucosamine-1-phosphotransferase |
| Niemann-Pick A*, B | Acid sphingomyelinase |
| Niemann-Pick C* | NPC-1 |
| Pompe* | Acid α-glucosidase |
| Sandhoff* | β-Hexosaminidase B |
| Sanfilippo A* | Heparan N-sulfatase |
| Sanfilippo B* | α-N-Acetylglucosaminidase |
| Sanfilippo C* | Acetyl-CoA: α-glucosaminide N-acetyltransferase |
| Sanfilippo D* | N-Acetylglucosamine-6-sulfate sulfatase |
| Schindler Disease* | α-N-Acetylgalactosaminidase |
| Schindler-Kanzaki | α-N-Acetylgalactosaminidase |
| Sialidosis | α-Neuramidase |
| Sly* | β-Glucuronidase |
| Tay-Sachs* | β-Hexosaminidase A |
| Wolman* | Acid Lipase |

*CNS involvement

The hallmark feature of LSD is the abnormal accumulation of metabolites in the lysosomes which leads to the formation of large numbers of distended lysosomes in the perikaryon. A major challenge to treating LSD (as opposed to treating a liver-specific enzymopathy) is the need to reverse lysosomal storage pathology in multiple separate tissues. Some LSDs can be effectively treated by intravenous infusion of the missing enzyme, known as enzyme replacement therapy (ERT). For example, Gaucher type 1 patients have only visceral disease and respond favorably to ERT with recombinant glucocerebrosidase (Cerezyme®, Genzyme Corp.). However, patients with metabolic disease that affects the CNS (e.g., type 2 or 3 Gaucher disease) do not respond to intravenous ERT because the replacement enzyme is prevented from entering the brain by the blood brain barrier (BBB). Furthermore, attempts to introduce a replacement enzyme into the brain by direct injection have been unsuccessful in part due to enzyme cytotoxicity at high local concentrations (unpublished observations) and limited parenchymal diffusion rates in the brain (Pardridge, Peptide Drug Delivery to the Brain, Raven Press, 1991).

Alzheimer's disease (AD) is a disorder affecting the central nervous system (CNS) characterized by the accumulation of amyloid β-peptide (Aβ) due to decreased Aβ catabolism. As Aβ accumulates, it aggregates into extracellular plaques, causing impairment of synaptic function and loss of neurons. The pathology leads to dementia, loss of coordination, and death.

Gene therapy is an emerging treatment modality for disorders affecting the CNS, including LSDs and Alzheimer's disease. In this approach, restoration of the normal metabolic pathway and reversal of pathology occurs by transducing affected cells with a vector carrying a healthy version or a modified version of the gene.

CNS gene therapy has been facilitated by the development of viral vectors capable of effectively infecting post-mitotic neurons. For a review of viral vectors for gene delivery to the CNS, see Davidson et al. (2003) Nature Rev., 4:353-364. Adeno-associated virus (AAV) vectors are considered optimal for CNS gene therapy because they have a favorable toxicity and immunogenicity profile, are able to transduce neuronal cells, and are able to mediate long-term expression in the CNS (Kaplitt et al. (1994) Nat. Genet., 8:148-154; Bartlett et al. (1998) Hum. Gene Ther., 9:1181-1186; and Passini et al. (2002) J. Neurosci., 22:6437-6446).

A therapeutic transgene product, e.g., an enzyme, can be secreted by transduced cells and subsequently taken up by other cells, in which it then alleviates pathology. This process is known as cross-correction (Neufeld et al. (1970) Science, 169:141-146). However, the correction of pathology, such as storage pathology in the context of LSD, is typically confined to the immediate vicinity of the injection site because of limited parenchymal diffusion of the injected vector and the secreted transgene product (Taylor et al. (1997) Nat. Med., 3:771-774; Skorupa et al. (1999) Exp. Neurol., 160:17-27). Thus, neuropathology affecting multiple brain regions requires widespread vector delivery, using multiple spatially distributed injections, especially in a large brain such as human. This significantly increases the risk of brain damage. In addition, some regions of the brain may be difficult to access surgically. Thus, other modes of vector transport within the CNS, besides diffusion, would be beneficial.

When administered at axonal endings, some viruses are internalized and transported retrogradely along the axon to the nucleus. Neurons in one brain region are interconnected by axons to distal brain regions thereby providing a transport system for vector delivery. Studies with adenovirus, HSV, and pseudo-rabies virus have utilized trafficking properties of these viruses to deliver genes to distal structures within the brain (Soudas et al. (2001) FASEB J., 15:2283-2285; Breakefield et al. (1991) New Biol., 3:203-218; and deFalco et al. (2001) Science, 291:2608-2613).

Several groups have reported that the transduction of the brain by AAV serotype 2 (AAV2) is limited to the intracranial injection site (Kaplitt et al. (1994) Nat. Genet., 8:148-154; Passini et al. (2002) J. Neurosci., 22:6437-6446; and Chamberlin et al. (1998) Brain Res., 793:169-175). One recent report suggests that retrograde axonal transport of AAV2 can also occur in select circuits of the normal rat brain (Kaspar et al. (2002) Mol. Ther., 5:50-56). However, it is not known what specific parameters were responsible for the observed axonal transport, and whether sufficient and effective axonal transport would occur in a diseased neuron that is in a state of cellular dysfunction. Indeed, lesions observed in LSD neurons have been reported to interfere with or even block axonal transport (reviewed in Walkley (1998) Brain Pathol., 8:175-193), suggesting that disease-compromised neurons would not support trafficking of AAV along their axons.

Therefore, there is a need in the art to develop new therapeutic methods for treating metabolic disorders that affect the CNS.

SUMMARY OF THE INVENTION

The invention provides methods and compositions for treating or preventing metabolic disorders, such as lysosomal storage diseases (LSD) or abnormal cholesterol storage function that are characterized by or associated with a risk of diminution of CNS function.

The invention provides methods and compositions for treating or preventing disorders affecting the central nervous system (CNS), such as Alzheimer's disease that are characterized by or associated with a risk of diminution of CNS function.

The invention further provides methods for minimally invasive targeted delivery of a transgene to select regions in the brain of an affected subject.

Additional advantages of the invention will be set forth in part in the following description, and in part will be understood from the description, or may be learned by practice of the invention.

Acid sphingomyelinase (ASM) knockout mice, a model of Niemann-Pick Type A disease, were administered an AAV2 vector carrying the human ASM gene (AAV-ASM) by a single intracranial injection into one hemisphere of the brain. The present invention is based, in part, on the discovery and demonstration that the injection of high titer AAV-ASM into the diseased brain results in AAV-ASM expression within multiple distal sites in a pattern consistent with the topographical organization of the projection neurons that innervate the injection site. The invention is further based, in part, on the discovery and demonstration of extensive correction of lysosomal storage pathology at the injection site and distal sites to which AAV-ASM was transported and where ASM was expressed.

In another aspect, the invention provides a method to correct cholesterol storage pathology and initiate functional recovery in the ASMKO mouse after unilateral or alternatively, bilateral injection within the deep cerebellar nuclei.

Further provided are the above-noted methods wherein the transgene is delivered in a recombinant AAV vector selected from the group consisting of AAV2/1, AAV2/2, AAV2/5, AAV2/7 and AAV2/8 serotype. For the purpose of illustration only, the recombinant vectors encoded functional human ASM protein in a mouse model.

Accordingly, in one aspect, the present invention provides methods for treating neurometabolic disorders in mammals. The populations treated by the methods of the invention include, but are not limited to, patients having or at risk for developing a LSD, such as disorders listed in Table 1, particularly, if such disease affects the CNS. In an illustrative embodiment, the disease is Niemann-Pick A disease and/or the secondary cholesterol storage pathology commonly associated with NPA.

In one aspect, the disclosed methods include administering to the CNS of an afflicted subject an AAV viral vector carrying a transgene encoding a therapeutic product and allowing the transgene to be expressed within the CNS distally from the administration site at a therapeutic level. In addition, the vector may comprise a polynucleotide encoding for a biologically active molecule effective to treat the CNS disorder. Such biologically active molecules may comprise peptides including but not limited to native or mutated versions of full-length proteins, native or mutated versions of protein fragments, synthetic polypeptides, antibodies, and antibody fragments such as Fab' molecules. Biologically active molecules may also comprise nucleotides including single-stranded or double-stranded DNA polynucleotides and single-stranded or double-stranded RNA polynucleotides. For a review of exemplary nucleotide technologies that may be used in the practice of the methods disclosed herein, see Kurreck, (2003) J., Eur. J. Biochem. 270, 1628-1644 [antisense technologies]; Yu et al., (2002) PNAS 99(9), 6047-6052 [RNA interference technologies]; and Elbashir et al., (2001) Genes Dev., 15(2):188-200 [siRNA technology].

In an illustrative embodiment, the administration is accomplished by direct intraparenchymal injection of a high titer AAV vector solution into the diseased brain. Thereafter the transgene is expressed distally, contralaterally or ipsilaterally, to the administration site at a therapeutic level at least 2, 3, 5, 8, 10, 15, 20, 25, 30, 35, 40, 45, or 50 mm from the administration site.

In another aspect, the invention also provides a method of delivering a recombinant AAV genome to the nucleus of a disease-compromised neuron in vivo. In some embodiments, the cellular pathology exhibited by the neuron is that of a lysosomal storage disease such as disorders listed in Table 1. In an illustrative embodiment, the disease is Niemann-Pick A disease. In other embodiments, the cellular pathology exhibited is that of Alzheimer's disease. The method of delivering a recombinant AAV genome to the nucleus of a disease-compromised neuron comprises contacting an axonal ending of the disease-compromised neuron with a composition comprising an AAV viral particle comprising the recombinant AAV genome and allowing the viral particle to be endocytosed and retrogradely transported intracellularly along the axon to the nucleus of the neuron. The concentration of the vector in the composition is at least:
(a) 5, 6, 7, 8, 8.4, 9, 9.3, 10, 15, 20, 25, or 50 ($\times 10^{12}$ gp/ml);
(b) 5, 6, 7, 8, 8.4, 9, 9.3, 10, 15, 20, 25, or 50 ($\times 10^9$ tu/ml);

or (c) 5, 6, 7, 8, 8.4, 9, 9.3, 10, 15, 20, 25, or 50 ($\times 10^{10}$ iu/ml). In certain embodiments, the neuron is a projection neuron and/or the distance of the axonal ending to the nucleus of the neuron is at least 2, 3, 5, 8, 10, 15, 20, 25, 30, 35, 40, 45, or 50 mm.

This invention provides methods and compositions to deliver a transgene to the spinal cord and/or the brainstem region of a subject by administering a recombinant neurotropic viral vector containing the transgene to at least one region of the deep cerebellar nuclei (DCN) region of the subject's brain. The viral delivery is under conditions that favor expression of the transgene in the spinal cord and/or the brainstem region. In an illustrative embodiment, the disease is Niemann-Pick A disease. In other embodiments, the cellular pathology exhibited is that of Alzheimer's disease.

In another aspect, the invention provides methods and compositions to deliver a transgene to a subject's spinal cord by administering a recombinant neurotropic viral vector containing the transgene to the motor cortex region of the subject's brain. The delivery of the viral vector is under conditions that favor expression of the transgene in the spinal cord. Viral vectors administered to the motor cortex region are internalized by motor neurons via their cell body region and the transgene is expressed. The expressed transgene may then undergo anterograde transport to the axon terminal portion of the motor neuron, which is present in the spinal cord. Due to the nature of the motor cortex, viral vectors administered to this region of the brain may also be internalized by axon terminals of motor neurons. The viral vector also may undergo retrograde transport along the motor neuron's axon and be expressed in the cell body of the motor neuron. In an illustrative embodiment, the disease is Niemann-Pick A disease. In other embodiments, the cellular pathology exhibited is that of Alzheimer's disease.

In another aspect, the invention provides a method of delivering a therapeutic transgene product to a target cell of the CNS, which is a neuron or a glial cell, in a mammal afflicted with a neurometabolic disorder, e.g., an LSD that affects the CNS. The method includes contacting an axonal ending of a neuron with a composition containing an AAV vector carrying at least a part of a gene encoding a therapeutic transgene product, allowing the viral particle to be endocytosed and retrogradely transported intracellularly along the axon to the nucleus of the neuron; allowing the therapeutic transgene product to be expressed and secreted by the neuron, and allowing the target cell to uptake the therapeutic transgene product, wherein the therapeutic transgene product thereby alleviates pathology in the target cell. In certain embodiments, the concentration of the vector in the composition is at least: (a) 5, 6, 7, 8, 8.4, 9, 9.3, 10, 15, 20, 25, or 50 ($\times 10^{12}$ gp/ml); (b) 5, 6, 7, 8, 8.4, 9, 9.3, 10, 15, 20, 25, or 50 ($\times 10^{9}$ to/ml); or (c) 5, 6, 7, 8, 8.4, 9, 9.3, 10, 15, 20, 25, or 50 ($\times 10^{19}$ iu/ml).

In the methods of the invention, the therapeutic transgene encodes a biologically active molecule, expression of which in the CNS results in at least partial correction of neuropathology. In some embodiments, the therapeutic transgene product is a lysosomal hydrolase. In an illustrative embodiment, the lysosomal hydrolase is ASM. In other embodiments, the therapeutic transgene is a metalloendopeptidase, e.g., neprilysin.

It is to be understood that both the foregoing general description and the following detailed description are exemplary and explanatory only and are not restrictive of the invention as claimed.

BRIEF DESCRIPTION OF THE FIGURES

FIGS. 6A through 6E show human ASM immunopositive staining in sagittal cerebellar sections following injection of different AAV serotype vectors [(A)2/1, (B)2/2, (C)2/5, (D)2/7 and (E)2/8] encoding for human ASM into the deep cerebellar nuclei of ASMKO mice.

FIGS. 9A through G show calbindin immunopositive staining in sagittal cerebellar sections following injection of different AAV serotype vectors [(A)2/1, (B)2/2, (C)2/5, (D)2/7 and (E)2/8] encoding for human ASM into the deep cerebellar nuclei of ASMKO mice.

FIG. 13B illustrates the connections between the deep cerebellar nuclei regions (medial, interposed, and lateral) and the brainstem regions (midbrain, pons, and medulla). The connections are represented by arrows, which start at the cell body region of a neuron and end at the axon terminal region of the neuron. For example, the three regions of the DCN each have neurons with cell bodies that send axons that terminate in the cervical region of the spinal cord while the cervical region of the spinal cord has cell bodies that send axons that terminate in either the medial or interposed regions of the DCN.

DETAILED DESCRIPTION OF THE INVENTION

Figure 1A:
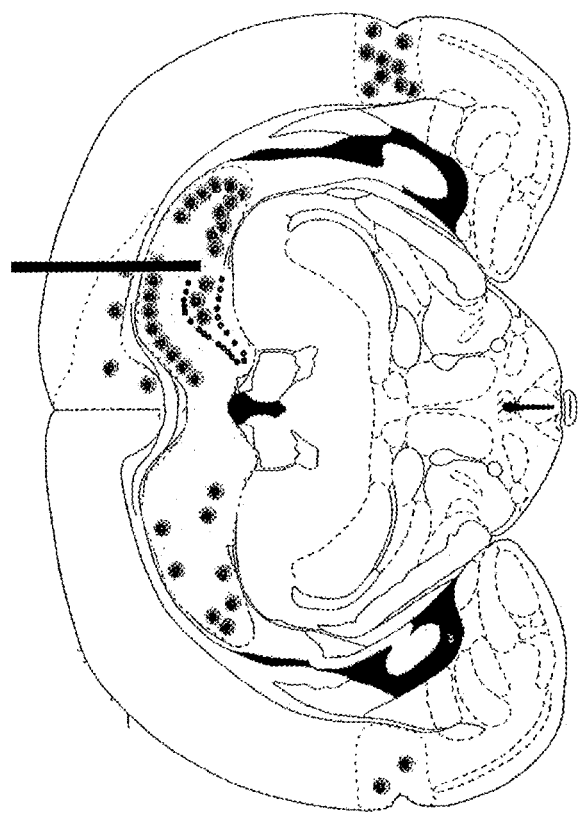
FIG. 1A depicts a representation of a cross-section of the ASMKO mouse brain, at 5 or 15 weeks following a 2 µl injection of high titer ($9.3 \times 10^{12}$ gp/ml) AAV-ASM into the hippocampus. The site of injection is shown by a vertical line; ASM mRNA expression, as detected by in situ hybridization, is represented the smaller circles; and ASM protein expression, as detected by immunohistochemical staining, is represented by the larger shaded circles. The expression pattern resulted in an extensive area of reversal of pathology (represented by the light shading) in the hippocampus and cortical regions in both hemispheres of the brain.

In order that the present invention may be more readily understood, certain terms are first defined. Additional definitions are set forth throughout the detailed description.

The term "transgene" refers to a polynucleotide that is introduced into a cell of and is capable of being translated and/or expressed under appropriate conditions and confers a desired property to a cell into which it was introduced, or otherwise leads to a desired therapeutic outcome.

The terms "genome particles (gp)," or "genome equivalents," as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) Hum. Gene Ther., 10:1031-1039; Veldwijk et al. (2002) Mol. Ther., 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) J. Virol., 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) Exp. Neurobiol., 144:113-124; or in Fisher et al. (1996) J. Virol., 70:520-532 (LFU assay).

The terms "therapeutic," "therapeutically effective amount," and their cognates refer to that amount of a compound that results in prevention or delay of onset or amelioration of symptoms of in a subject or an attainment of a desired biological outcome, such as correction of neuropathology, e.g., cellular pathology associated with a lysosomal storage disease such as that described herein or in Walkley (1998) Brain Pathol., 8:175-193. The term "therapeutic correction" refers to that degree of correction that results in prevention or delay of onset or amelioration of symptoms in a subject. The effective amount can be determined by methods well-known in the art and as described in the subsequent sections.

Methods and Compositions

ASMKO mice are an accepted model of types A and B Niemann-Pick disease (Horinouchi et al. (1995) Nat. Genetics, 10:288-293; Jin et al. (2002) J. Clin. Invest., 109:1183-1191; and Otterbach (1995) Cell, 81:1053-1061). Niemann-Pick disease (NPD) is classified as a lysosomal storage disease and is an inherited neurometabolic disorder characterized by a genetic deficiency in acid sphingomyelinase (ASM; sphingomyelin cholinephosphohydrolase, EC 3.1.3.12). The lack of functional ASM protein results in the accumulation of sphingomyelin substrate within the lysosomes of neurons and glia throughout the brain. This leads to the formation of large numbers of distended lysosomes in the perikaryon, which are a hallmark feature and the primary cellular phenotype of type A NPD. The presence of distended lysosomes correlates with the loss of normal cellular function and a progressive neurodegenerative course that leads to death of the affected individual in early childhood (The Metabolic and Molecular Bases of Inherited Diseases, eds. Scriver et al., McGraw-Hill, New York, 2001, pp. 3589-3610). Secondary cellular phenotypes (e.g., additional metabolic abnormalities) are also associated with this disease, notably the high level accumulation of cholesterol in the lysosomal compartment. Sphingomyelin has strong affinity for cholesterol, which results in the sequestering of large amounts of cholesterol in the lysosomes of ASMKO mice and human patients (Leventhal et al. (2001) J. Biol. Chem., 276:44976-44983; Slotte (1997) Subcell. Biochem., 28:277-293; and Viana et la. (1990) J. Med. Genet., 27:499-504.)

The present invention is based, in part, on the discovery and demonstration that an intrahippocampal injection of high titer AAV-ASM into the diseased brains of ASMKO mice results in expression of ASM mRNA and protein distally from the injection site in a pattern consistent with the topographical organization of the projection neurons that innervate the injection site. In addition to robust expression at the site of injection, ASM mRNA and protein are also detected in several distal regions outside of the ipsilateral (injected) hippocampus, specifically, in the contralateral hippocampal dentate gyrus and CA3, and the medial septum and entorhinal cortex. The invention is further based, in part, on the discovery and demonstration of the extensive correction of lysosomal storage pathology at the distal sites thereby allowing a larger volume of correction via a smaller number of injection sites.

Accordingly, in one aspect, the present invention provides methods for treating neurometabolic disorders in mammals. The populations treated by the methods of the invention include, but are not limited to, patients having or at risk for developing a neurometabolic disorder, e.g., a LSD, such as diseases listed in Table 1, particularly, if such a disease affects the CNS. In an illustrative embodiment, the disease is type A Niemann-Pick disease. In certain embodiments, neurometabolic disorders may exclude Alzheimer's, Parkinson, Huntington, Tay Sachs, Lesch-Nyan, and Creutzfeldt-Jakob diseases. However, methods of the invention utilizing a metalloendopeptidase as a therapeutic transgene, are specifically useful to the treatment of Alzheimer's disease and amyloid-related disorders.

In some embodiments, the method of treating a neurometabolic disorder comprises administration of a high titer AAV vector carrying a therapeutic transgene so that the transgene product is expressed at a therapeutic level in a second site within the CNS distal to the first site. In some embodiments, the viral titer of the composition is at least: (a) 5, 6, 7, 8, 8.4, 9, 9.3, 10, 15, 20, 25, or 50 ($\times 10^{12}$ gp/ml); (b) 5, 6, 7, 8, 8.4, 9, 9.3, 10, 15, 20, 25, or 50 ($\times 10^9$ to/ml); or (c) 5, 6, 7, 8, 8.4, 9, 9.3, 10, 15, 20, 25, or 50 ($\times 10^{10}$ iu/ml). In further embodiments, the administration is accomplished by direct intraparenchymal injection of a high titer AAV vector solution into the diseased brain, thereafter the transgene is expressed distally, contralaterally or ipsilaterally, to the administration site at a therapeutic level at least 2, 3, 5, 8, 10, 15, 20, 25, 30, 35, 40, 45, or 50 mm from the administration site.

The distance between the first and the second sites is defined as the minimal distance region between the site of administration (first site) and the boundary of the detectable transduction of the distal site (second site) as measured using procedures known in the art or as described in the Examples, e.g., in situ hybridization. Some neurons in the CNS of larger mammals may span large distances by virtue of their axonal projections. For example, in humans, some axons may span a distance of 1000 mm or greater. Thus, in various methods of the invention, AAV can be axonally transported along the entire length of the axon at such a distance to reach and transduce the parent cell body.

A site of vector administration within the CNS is chosen based on the desired target region of neuropathology and the topology of brain circuits involved so long as an administration site and the target region have axonal connections. The target region can be defined, for example, using 3-D sterotaxic coordinates. In some embodiments, the administration site is chosen so that at least 0.1, 0.5, 1, 5, or 10% of the total amount of vector injected is delivered distally at the target region of at least 1, 200, 500, or 1000 mm$^3$. An administration site may be localized in a region innervated by projection neurons connecting distal regions of the brain. For example, the substantia nigra and bventral tegmental area send dense projections to the caudate and putamen (collectively known as the striatum). Neurons within the substantia nigra and ventral tegmentum can be targeted for transduction by retrograde transport of AAV following injection into the striatum. As another example, the hippocampus receives well-defined, predictable axonal projections from other regions of the brain. Other administration sites may be localized, for example, in the spinal cord, brainstem (medulla and pons), mesencephalon, cerebellum (including the deep cerebellar nuclei), diencephalon (thalamus, hypothalamus), telencephalon (corpus striatum, cerebral cortex, or, within the cortex, the occipital, temporal, parietal or frontal lobes), or combinations thereof.

For identification of structures in the human brain, see, e.g., The Human Brain: Surface, Three-Dimensional Sectional Anatomy With MRI, and Blood Supply, 2nd ed., eds. Deuteron et al., Springer Vela, 1999; Atlas of the Human Brain, eds. Mai et al., Academic Press; 1997; and Co-Planar Sterotaxic Atlas of the Human Brain: 3-Dimensional Proportional System: An Approach to Cerebral Imaging, eds. Tamarack et al., Thyme Medical Pub., 1988. For identification of structures in the mouse brain, see, e.g., The Mouse Brain in Sterotaxic Coordinates, 2nd ed., Academic Press, 2000. If desired, the human brain structure can be correlated to similar structures in the brain of another mammal. For example, most mammals, including humans and rodents, show a similar topographical organization of the entorhinal-hippocampus projections, with neurons in the lateral part of both the lateral and medial entorhinal cortex projecting to the dorsal part or septal pole of the hippocampus, whereas the projection to the ventral hippocampus originates primarily from neurons in medial parts of the entorhinal cortex (Principles of Neural Science, 4th ed., eds Kandel et al., McGraw-Hill, 1991; The Rat Nervous System, 2nd ed., ed.

Paxinos, Academic Press, 1995). Furthermore, layer II cells of the entorhinal cortex project to the dentate gyrus, and they terminate in the outer two-thirds of the molecular layer of the dentate gyrus. The axons from layer III cells project bilaterally to the cornu ammonis areas CA1 and CA3 of the hippocampus, terminating in the stratum lacunose molecular layer.

The second (target) site can be located any region of the CNS, including the brain and the spinal cord, that contains a neurons that project to the first (administration) site. In some embodiments, the second site is in a region of the CNS chosen from the substantia nigra, the medulla oblongata, or the spinal cord.

To deliver the vector specifically to a particular region of the central nervous system, especially to a particular region of the brain, it may be administered by sterotaxic microinjection. For example, on the day of surgery, patients will have the sterotaxic frame base fixed in place (screwed into the skull). The brain with sterotaxic frame base (MRI-compatible with fiduciary markings) will be imaged using high resolution MRI. The MRI images will then be transferred to a computer that runs stereotaxic software. A series of coronal, sagittal and axial images will be used to determine the target site of vector injection, and trajectory. The software directly translates the trajectory into 3-dimensional coordinates appropriate for the stereotaxic frame. Burr holes are drilled above the entry site and the stereotaxic apparatus localized with the needle implanted at the given depth. The vector in a pharmaceutically acceptable carrier will then be injected. The AAV vector is then administered by direct injection to the primary target site and retrogradely transported to distal target sites via axons. Additional routes of administration may be used, e.g., superficial cortical application under direct visualization, or other non-stereotaxic application.

The total volume of material to be administered, and the total number of vector particles to be administered, will be determined by those skilled in the art based upon known aspects of gene therapy. Therapeutic effectiveness and safety can be tested in an appropriate animal model. For example, a variety of well-characterized animal models exist for LSDs, e.g., as described herein or in Watson et al. (2001) Methods Mol. Med., 76:383-403; or Jeyakumar et al. (2002) Neuropath. Appl. Neurobiol., 28:343-357.

In experimental mice, the total volume of injected AAV solution is for example, between 1 to 5 µl. For other mammals, including the human brain, volumes and delivery rates are appropriately scaled. For example, it has been demonstrated that volumes of 150 µl can be safely injected in the primate brain (Janson et al. (2002) Hum. Gene Ther., 13:1391-1412). Treatment may consist of a single injection per target site, or may be repeated along the injection tract, if necessary. Multiple injection sites can be used. For example, in some embodiments, in addition to the first administration site, a composition comprising AAV carrying a transgene is administered to another site which can be contralateral or ipsilateral to the first administration site.

In another aspect, the invention provides a method of delivering a recombinant AAV genome via retrograde axonal transport to the nucleus of a disease-compromised neuron in vivo. In some embodiments, the cellular pathology exhibited by a neuron is that of a LSD such as listed in Table 1 (see, e.g., Walkley (1998) Brain Pathol., 8:175-193). In an illustrative embodiment, the disease is Niemann-Pick A disease. The method of delivering a recombinant AAV genome to the nucleus of a disease-compromised neuron comprises contacting an axonal ending of a disease-compromised neuron with a composition comprising an AAV viral particle comprising the recombinant AAV genome and allowing the viral particle to be endocytosed and retrogradely transported intracellulary along the axon to the nucleus of the neuron, wherein the concentration of AAV genomes in the composition is at least: (a) 5, 6, 7, 8, 8.4, 9, 9.3, 10, 15, 20, 25, or 50 ($\times 10^{12}$ gp/ml); (b) 5, 6, 7, 8, 8.4, 9, 9.3, 10, 15, 20, 25, or 50 ($\times 10^{9}$ tu/ml); or (c) 5, 6, 7, 8, 8.4, 9, 9.3, 10, 15, 20, 25, or 50 ($\times 10^{19}$ iu/ml). In certain embodiments, the neuron is a projection neuron and/or the distance from the axonal ending to the nucleus of the neuron is at least 2, 3, 5, 8, 10, 15, 20, 25, 30, 35, 40, 45, or 50 mm. In various embodiments, the AAV genome is transported along the entire length of the axon, at distances varying depending on the axon length. In humans, these distances may be as much as 1000 mm or greater.

In another aspect, the invention provides a method of delivering a transgene product to a target cell of the CNS, which is a neuron or a glial cell, in a mammal afflicted with a disorder, for example an LSD as listed in Table 1. The method comprises contacting an axonal ending of a neuron with a composition comprising an AAV vector carrying at least a part of a gene encoding a therapeutic transgene product; allowing the viral particles to be endocytosed and retrogradely transported intracellularly along the axon to the nucleus of the neuron; allowing the transgene product to be expressed and secreted by the neuron; and allowing a second cell to uptake the transgene product, wherein the transgene product thereby alleviates pathology in the second cell. In some embodiments the concentration of the AAV vector in the composition is at least: (a) 5, 6, 7, 8, 8.4, 9, 9.3, 10, 15, 20, 25, or 50 ($\times 10^{12}$ gp/ml); (b) 5, 6, 7, 8, 8.4, 9, 9.3, 10, 15, 20, 25, or 50 ($\times 10^{9}$ tu/ml); or (c) 5, 6, 7, 8, 8.4, 9, 9.3, 10, 15, 20, 25, or 50 ($\times 10^{10}$ iu/ml). For example, lysosomal hydrolases can be secreted by transduced cells and subsequently taken up by another cell via mannose-6-phosphate receptor-mediated endocytosis, the second cell being transduced or non-transduced (Sando et al. (1977) Cell, 12:619-627; Taylor et al. (1997) Nat. Med., 3:771-774; Miranda et al. (2000) Gene Ther., 7:1768-1776; and Jin et al. (2002) J. Clin. Invest., 109:1183-1191).

In the methods of the invention, AAV of any serotype can be used so long as the vector is capable of undergoing retrograde axonal transport in a disease-compromised brain. The serotype of the viral vector used in certain embodiments of the invention is selected from the group consisting from AAV1, AAV2, AAV3, AAV4, AAV5, AAV6, AAV7, and AAV8 (see, e.g., Gao et al. (2002) PNAS, 99:11854-11859; and Viral Vectors for Gene Therapy: Methods and Protocols, ed. Machida, Humana Press, 2003). Other serotype besides those listed herein can be used. Furthermore, pseudotyped AAV vectors may also be utilized in the methods described herein. Pseudotyped AAV vectors are those which contain the genome of one AAV serotype in the capsid of a second AAV serotype; for example, an AAV vector that contains the AAV2 capsid and the AAV1 genome or an AAV vector that contains the AAV5 capsid and the AAV 2 genome. (Auricchio et al., (2001) Hum. Mol. Genet., 10(26):3075-81.) However, AAV5 may be specifically excluded from the methods of the invention utilizing a metalloendopeptidase, e.g., neprilysin, as a therapeutic transgene.

AAV vectors are derived from single-stranded (ss) DNA parvoviruses that are nonpathogenic for mammals (reviewed in Muzyscka (1992) Curr. Top. Microb. Immunol., 158:97-129). Briefly, AAV-based vectors have the rep and cap viral genes that account for 96% of the viral genome removed, leaving the two flanking 145-basepair (bp) inverted terminal repeats (ITRs), which are used to initiate viral DNA replication, packaging and integration. In the absence of helper virus, wild-type AAV integrates into the human host-cell genome with preferential site-specificity at chromosome 19q 13.3 or it may remain expressed episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, may nearly double this limit.

In an illustrative embodiment, AAV is AAV2 or AAV1. Adeno-associated virus of many serotypes, especially AAV2, have been extensively studied and characterized as gene therapy vectors. Those skilled in the art will be familiar with the preparation of functional AAV-based gene therapy vectors. Numerous references to various methods of AAV production, purification and preparation for administration to human subjects can be found in the extensive body of published literature (see, e.g., Viral Vectors for Gene Therapy: Methods and Protocols, ed. Machida, Humana Press, 2003). Additionally, AAV-based gene therapy targeted to cells of the CNS has been described in U.S. Pat. Nos. 6,180,613 and 6,503,888.

In certain methods of the invention, the vector comprises a transgene operably linked to a promoter. The transgene encodes a biologically active molecule, expression of which in the CNS results in at least partial correction of neuropathology. In some embodiments, the transgene encodes a lysosomal hydrolase. In an illustrative embodiment, the lysosomal hydrolase is ASM. The genomic and functional cDNA sequences of human ASM have been published (see, e.g., U.S. Pat. Nos. 5,773,278 and 6,541,218). Other lysosomal hydrolases can be used for appropriate diseases, for example, as listed in Table 1.

The invention further provides methods of treating Alzheimer's disease in mammals, including humans. In such methods, the transgene encodes a metalloendopeptidase. The metalloendopeptidase can be, for example, the amyloid-beta degrading enzyme neprilysin (EC 3.4.24.11; sequence accession number, e.g., P08473 (SWISS-PROT)), the insulin-degrading enzyme insulysin (EC 3.4.24.56; sequence accession number, e.g., P14735 (SWISS-PROT)), or thimet oligopeptidase (EC 3.4.24.15; sequence accession number, e.g., P52888 (SWISS-PROT)).

The level of transgene expression in eukaryotic cells is largely determined by the transcriptional promoter within the transgene expression cassette. Promoters that show long-term activity and are tissue- and even cell-specific are used in some embodiments. Nonlimiting examples of promoters include, but are not limited to, the cytomegalovirus (CMV) promoter (Kaplitt et al. (1994) Nat. Genet., 8:148-154), CMV/human β3-globin promoter (Mandel et al. (1998) J. Neurosci., 18:4271-4284), GFAP promoter (Xu et al. (2001) Gene Ther., 8:1323-1332), the 1.8-kb neuron-specific enolase (NSE) promoter (Klein et al. (1998) Exp. Neurol., 150:183-194), chicken beta actin (CBA) promoter (Miyazaki (1989) Gene, 79:269-277) and the␤-glucuronidase (GUSB) promoter (Shipley et al. (1991) Genetics, 10:1009-1018). To prolong expression, other regulatory elements may additionally be operably linked to the transgene, such as, e.g., the Woodchuck Hepatitis Virus Post-Regulatory Element (WPRE) (Donello et al. (1998) J. Virol., 72, 5085-5092) or the bovine growth hormone (BGH) polyadenylation site.

For some CNS gene therapy applications, it will be necessary to control transcriptional activity. To this end, pharmacological regulation of gene expression with AAV vectors can been obtained by including various regulatory elements and drug-responsive promoters as described, for example, in Habermaet al. (1998) Gene Ther., 5:1604-16011; and Ye et al. (1995) Science, 283:88-91.

High titer AAV preparations can be produced using techniques known in the art, e.g., as described in U.S. Pat. No. 5,658,776 and Viral Vectors for Gene Therapy: Methods and Protocols, ed. Machida, Humana Press, 2003.

The following examples provide illustrative embodiments of the invention. One of ordinary skill in the art will recognize the numerous modifications and variations that may be performed without altering the spirit or scope of the present invention. Such modifications and variations are encompassed within the scope of the invention. The examples do not in any way limit the invention.

EXAMPLES

Titration of Recombinant Vectors

AAV vector titers were measured according to genome copy number (genome particles per milliliter). Genome particle concentrations were based on Taqman® PCR of the vector DNA as previously reported (Clark et al. (1999) Hum. Gene Ther., 10:1031-1039; Veldwijk et al. (2002) Mol. Ther., 6:272-278). Briefly, purified AAV-ASM was treated with capsid digestion buffer (50 mM Tris-HCl pH 8.0, 1.0 mM EDTA, 0.5% SDS, 1.0 mg/ml proteinase K) at 50° C. for 1 hour to release vector DNA. DNA samples were put through a polymerase chain reaction (PCR) with primers that anneal to specific sequences in the vector DNA, such as the promoter region, transgene, or the poly A sequence. The PCR results were then quantified by a Real-time Taqman® software, such as that provided by the Perkin Elmer-Applied Biosystems (Foster City, CA) Prism 7700 Sequence Detector System.

Vectors carrying an assayable marker gene such as the β-galactosidase or green fluorescent protein gene (GFP) can be titered using an infectivity assay. Susceptible cells (e.g., HeLa, or COS cells) are transduced with the AAV and an assay is performed to determine gene expression such as staining of β-galactosidase vector-transduced cells with X-gal (5-bromo-4chloro-3-indolyl-β-D-galactopyranoside) or fluorescence microscopy for GFP-transduced cells. For example, the assay is performed as follows: $4 \times 10^4$ HeLa cells are plated in each well of a 24-well culture plate using normal growth media. After attachment, i.e., about 24 hours later, the cells are infected with Ad type 5 at a multiplicity of infection (MOI) of 10 and transduced with serial dilutions of the packaged vector and incubated at 37° C. One to three days later, before extensive cytopathic effects are observed, the appropriate assay is performed on the cells (e.g., X-gal staining or fluorescence microscopy). If a reporter gene such as β-galactosidase is used, the cells are fixed in 2% paraformaldehyde, 0.5% glutaraldehyde and stained for β-galactosidase activity using X-gal. Vector dilutions that give well-separated cells are counted. Each positive cell represents 1 transduction unit (tu) of vector.

Correction of LSD Pathology in the Mouse Brain

Ten-week old ASMKO mice contain significant NPD pathology in the central nervous system. Identification of homozygous recessive mutants was verified by PCR. Sixteen 10-week old ASMKO mice were anesthetized with isoflurane and mounted on a stereotaxic frame, an incision was made to expose the underlying skull, and a single drill hole was made over one hemisphere of each mouse. Two microliters of high titer ($9.3 \times 10^{12}$ gp/ml) AAV2-CMV-ASM (Targeted Genetics, Seattle, WA) were injected into the hippocampus at a final stereotaxic coordinate of 2.0 mm rostral of bregma, 1.5 mm right of midline, and 2.0 mm ventral to pial surface. This hippocampal coordinates ensured that the AAV2 vector was exposed to neurons of the dentate gyrus and of the cornu ammonis area 3 (CA3), as well as to axonal endings of projection neurons of the contralateral hippocampus, medial septum and entorhinal cortex. The injections were performed at a rate of 0.2 µl/minute, and a total of $1.86 \times 10^{10}$ genomic particles were administered into each brain.

Figure 10A:
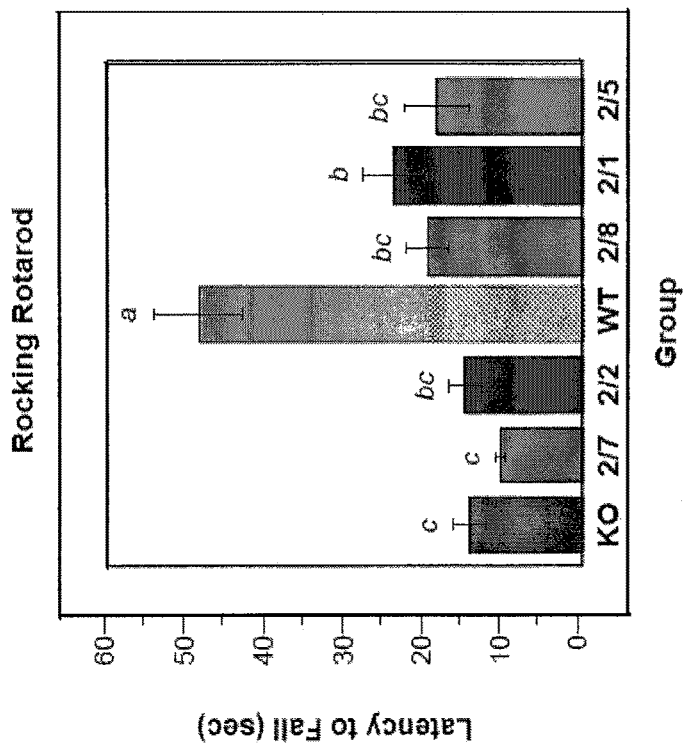
FIGS. 10A and 10B show accelerating and rocking rotarod performance (at 14 weeks of age) in ASMKO (injected with AAV-βgal), WT, and AAV-ASM treated ASMKO mice (n=8/group). Groups not connected by the same letter are significantly different. Mice injected with AAV2/1-ASM and AAV2/8-ASM demonstrated a significantly (p<0.0009) longer latency to fall than ASMKO mice injected with AAV2/1-βgal in the accelerating rotarod test. For the rocking rotarod test, mice injected with AA2/1-ASM demonstrated a significantly (p<0.0001) longer latency to fall than mice injected with AAV2/1-βgal.

Mice were tested by accelerating and rocking rotarod for motor function on the Smartrod (AccuScan) using methods known in the art and reproduced in Sleat et al. (2004) J. Neurosci. 24:9117-9126. FIGS. 10A/B and FIGS. 11A/B graphically show the results of rotarod tests as a measurement of recovery of motor function.

The mice were then sacrificed at either 5 (n=8) or 15 (n=8) weeks post injection (pi). Eight brains (n=4 each at 5 and 15 weeks pi) were analyzed for ASM mRNA and protein distribution, and for the reduction of the supraphysiologic levels of cholesterol in the lysosomes. The remaining 8 brains (n=4 each at 5 and 15 weeks pi) were processed for histopathology to analyze the correction of accumulated and distended lysosomes, which is the most direct and accurate method for determining reversal of storage pathology for LSDs.

Robust transduction was detected in the injected (ipsilateral) hippocampus at 5 and 15 weeks pi. The granule cell layer and hilus of the dentate gyrus, and the pyramidal and oriens cell layers of CA3 were extensively transduced by the AAV2 vector. This impressive pattern of transduction extended to other regions of the ipsilateral hippocampus, such as the subiculum and cornu ammonis area 1 (CA1) and 2 (CA2). Immunofluorescence with an anti-human ASM monoclonal antibody confirmed the presence of ASM protein in many cells. The overall protein pattern was similar to the mRNA pattern, with some additional localized spread of protein.

Figure 1C:
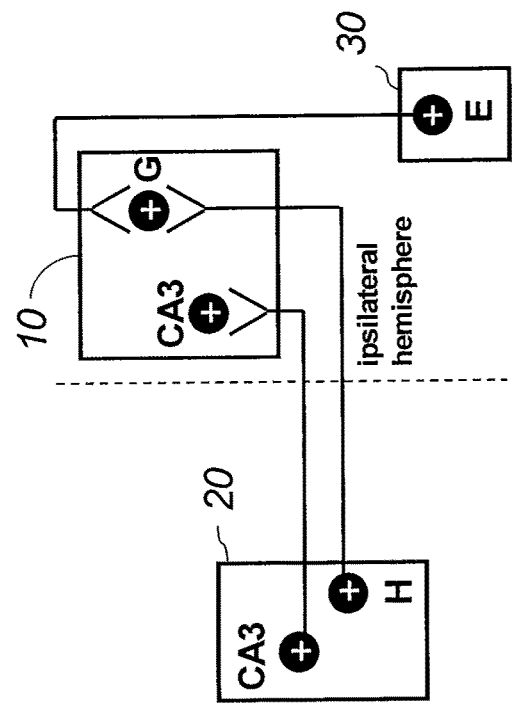
FIG. 1C is a schematic diagram showing the connections of the intrahippocampal and entorhinodentate circuits of the mouse brain. Injection into the hippocampus (10) results in infection and transduction of cell bodies located in the cornu ammonis area 3 (CA3) and in the dentate granule cell layer (G). In addition, a subset of the injected AAV vector infects the axonal endings of the projection neurons innervating the injection site, undergoes retrograde axonal transport, and delivers the transgene to the CA3 field (CA3) and hilus (H) in the contralateral part of the hippocampus (20), and ipsilaterally in the entorhinal cortex (30).
Figure 1B:
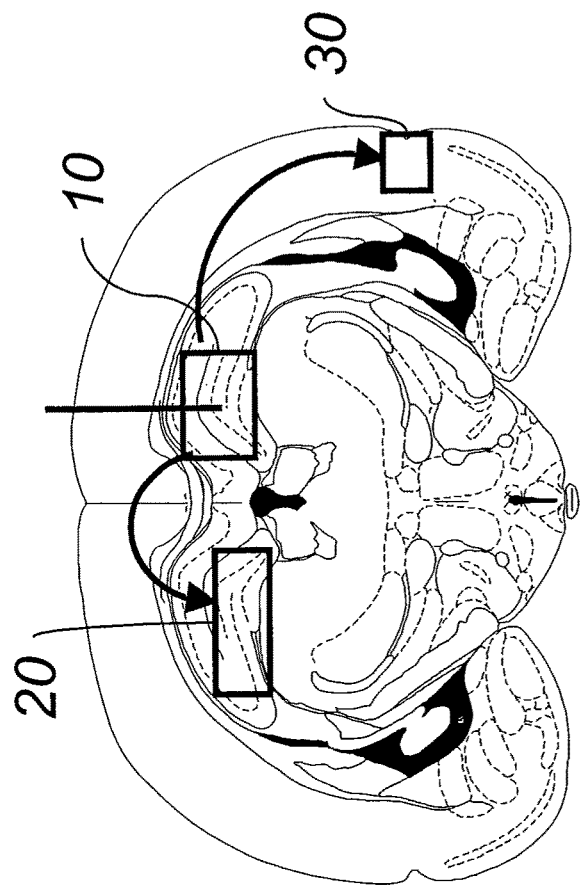
FIG. 1B depicts the axonal transport of AAV to distal regions of the mouse brain following a high titer AAV injection into the hippocampus as described for FIG. 1A. Injection into the hippocampus (10) resulted in axonal transport of the viral vector via the intrahippocampal circuit to the contralateral hippocampus (20) and via the entorhinodentate circuit to the entorhinal cortex (30). The site of injection is shown by a vertical line.
Figure 2A:
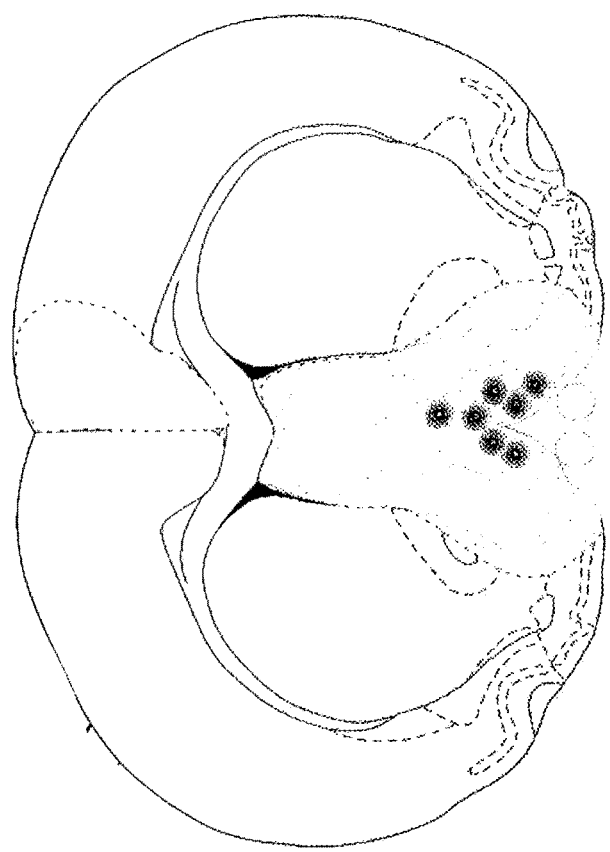
FIG. 2A depicts a representation of a cross-section of the ASMKO mouse brain, at 5 or 15 weeks following an intrahippocampal injection of high titer AAV-ASM as described in FIG. 1A. ASM mRNA expression, as detected by in situ hybridization, is represented by the smaller circles; and ASM protein expression, as detected by immunohistochemical staining, is represented by the larger shaded circles. The injection resulted in ASM mRNA and protein to be detected in the septum. This expression pattern resulted in an extensive area of reversal of pathology (represented by the light shading).
Figure 2C:
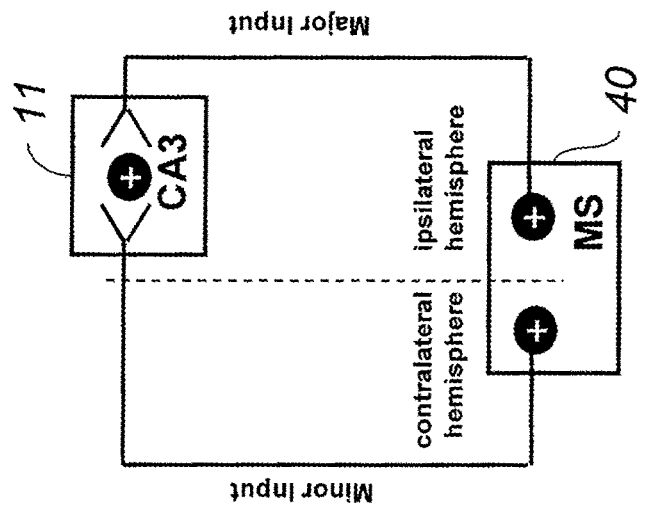
FIG. 2C is a schematic diagram showing the connections of the septohippocampal circuit. Injection into the hippocampus resulted in transduction to cell bodies located in the CA3 field (11). In addition, a subset of the AAV vector infects the axonal endings of the projection neurons innervating the injection site, undergoes retrograde axonal transport, and delivers the transgene to the medial septum (40).
Figure 2B:
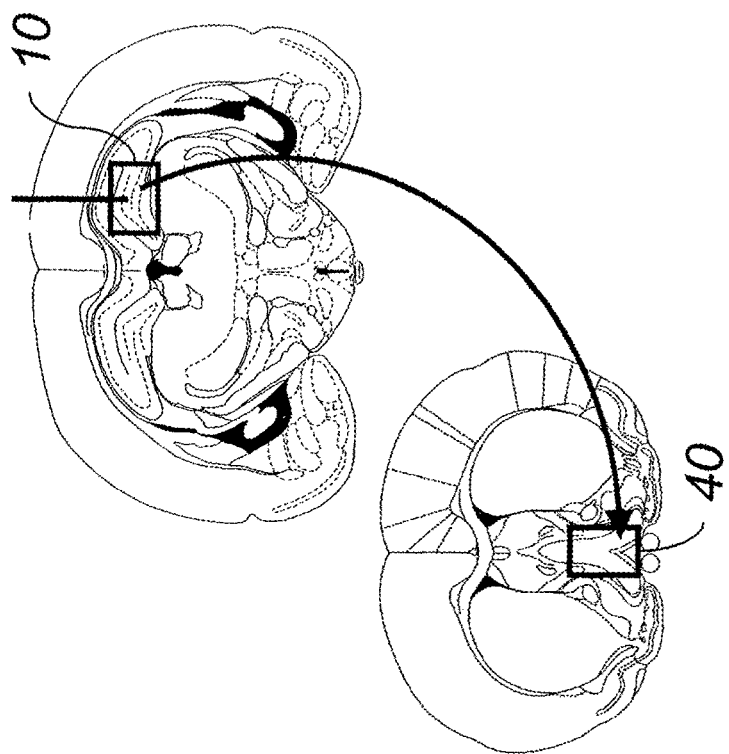
FIG. 2B depicts the axonal transport of AAV to distal regions of the mouse brain, following a high titer injection into the hippocampus as described in FIG. 1A. Injection into the hippocampus (10) resulted in axonal transport of the viral vector via the septohippocampal circuit from the injection site (represented by a vertical line) to the septum (40).

Human ASM mRNA and protein were also detected in regions outside of the ipsilateral hippocampus at both time points. The contralateral dentate gyrus and CA3, and the medial septum and entorhinal cortex were positive for in situ hybridization and immunofluorescence (FIGS. 1A and 2A). The pattern of transduction at these distal sites was consistent with the topographical organization of the projection neurons that innervate the injection site (FIGS. 1B and 2B). This demonstrated that AAV2 underwent retrograde axonal transport in the intrahippocampal, septohippocampal and entorhinodentate circuits of ASMKO brains, and that the viral vector was targeted to the nucleus following transport up the axons (FIGS. 1C and 2C). The pattern of transduction does not support parenchymal diffusion as the reason for AAV2 transport to these distal sites. If such diffusion had occurred, structures between the injected and distal sites would have been exposed to migrating virus. But these intermediate structures were negative for in situ hybridization. For example the striatum, which possesses a strong natural tropism for AAV2, was negative for gene transfer despite being in the direct path between the hippocampus and medial septum. Thus, gene transfer to the distal sites must have arisen by retrograde axonal transport, which indicates that an affected projection neuron can function as an effective highway transport system for AAV2 movement through a diseased brain.

The ability of ASM to reverse the cholesterol abnormalities in the ASMKO brain additionally was investigated. Filipin is an autofluorescent molecule isolated from *Streptomyces filipinensis* that binds to cholesterol complexes (Leventhal et al. (2001) J. Biol. Chem., 276:44976-44983; and Sarna et al. (2001) Eur. J. Neurosci., 13:1-9). Uninjected ASMKO brains had high levels of filipin staining due to these abundant cholesterol complexes, whereas normal mouse brains produced no filipin staining.

Injection of AAV2-CMV-ASM resulted in the complete loss of filipin staining throughout the entire ipsilateral and contralateral hippocampus, septum and entorhinal cortex at 5 and 15 weeks pi of ASMKO mice (FIGS. 1A and 2A). This was in stark contrast to uninjected age-matched ASMKO controls, where high levels of filipin staining were detected in these same structures. The loss of filipin staining in AAV2-injected brains demonstrates that a secondary cellular phenotype (e.g. metabolic defect) of ASM disease was corrected. This strongly suggests that ASM protein was targeted to the lysosome and interacted with the sphingomyelin-cholesterol complex. This interaction likely resulted in the release of cholesterol from sphingomyelin, and subsequent entry of cholesterol into its normal biological pathways (such as degradation or translocation to the plasma membrane (Leventhal et al. (2001) J. Biol. Chem., 276: 44976-44983)).

The loss of filipin staining was observed in all cell layers and subfields of the intrahippocampal, septohippocampal and entorhinodentate circuits. The area of cholesterol correction was far greater and more extensive than the ASM protein pattern. This indicates that, following retrograde axonal transport of AAV2, projection neurons may have functioned as "enzyme pumps" and secreted ASM protein into the surrounding tissue. Significantly, only a small amount of ASM is needed to have a therapeutic effect on cholesterol accumulation within ASMKO-affected cells, an amount below the detection limit of the immunofluorescent protocol.

Whether axonal transport of the AAV2-ASM vector results in the correction of the primary cellular phenotype of NPD also was evaluated. One-micron-thick histopathology brain sections demonstrated a remarkable reduction of accumulated and distended lysosomal pathology in AAV2-CMV-ASM-injected brains at 5 weeks pi (Table 2). Reversal of pathology resulting in partial or complete restoration of normal cellular architecture occurred in all regions of the ipsilateral and the contralateral hemispheres of the hippocampus. The medial septum and the entorhinal cortex also showed a substantial reduction in storage lesions. Similar to the filipin data, the number of cells corrected was greater and more widespread than the ASM protein pattern. Reversal of pathology was evident within regions known to project to the hippocampus including the intrahippocampal, septohippocampal and entorhinodentate circuits. Overall, the volume of correction was 30-35 $mm^3$ or more in the contralateral hippocampus, 5-8 $mm^3$ or more in the ipsilateral entorhinal cortex, 1-2 $mm^3$ or more in the contralateral entorhinal cortex, and 2-3 $mm^3$ or more in the medial septum. This further supports that axonal transport of the viral vector was responsible for this therapeutic effect, because nearby structures (that do not contribute to these circuits) would have been corrected if viral distribution was mediated merely by diffusion (see, "ipsilateral striatum" and "contralateral striatum" in Table 2).

To demonstrate that reversal of pathology was specific to ASM, an additional group of ASMKO mice was injected with a control vector carrying a reporter gene, AAV2-CMV-β-gal (n=2 each at 5 and 15 weeks pi), and processed for histopathology. In all four brains, cells remained inundated with distended lysosomes, and contained other abnormalities such as cytoplasmic swelling and disorganized cellular layers.

TABLE 2

| Brain Region | Untreated | AAV2-ASM Treated |
|---|---|---|
| Ipsilateral Hippocampus | | |
| CA1 Field | ++++ | + |
| CA3 Field | ++++ | + |
| Dentate Granule Cell Layer | ++++ | + |
| Hilus | ++++ | + |
| Contralateral Hippocampus | | |
| CA1 Field | ++++ | + |
| CA3 Field | ++++ | + |
| Dentate Granule Cell Layer | ++++ | + |
| Hilus | ++++ | + |
| Ipsilateral Entorhinal Cortex | ++++ | ++ |
| Contralateral Entorhinal Cortex | ++++ | +++ |
| Ipsilateral Medial Septum | ++++ | ++ |
| Contralateral Medial Septum | ++++ | ++ |
| Ipsilateral Striatum | ++++ | ++++ |
| Contralateral Striatum | ++++ | ++++ |

Figure 4:
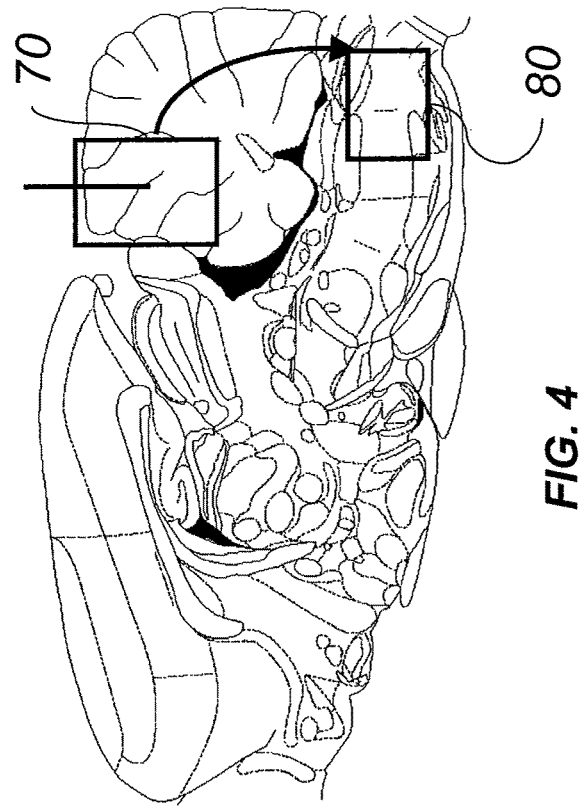
FIG. 4 depicts the axonal transport of AAV in the medullocerebellar circuit, following a high titer injection of AAV-ASM into the cerebellum (70) of the ASMKO mouse brain. Axonal transport of AAV2 occurs from the injection site (represented by a vertical line) to the medulla oblongata (80).
Figure 3:
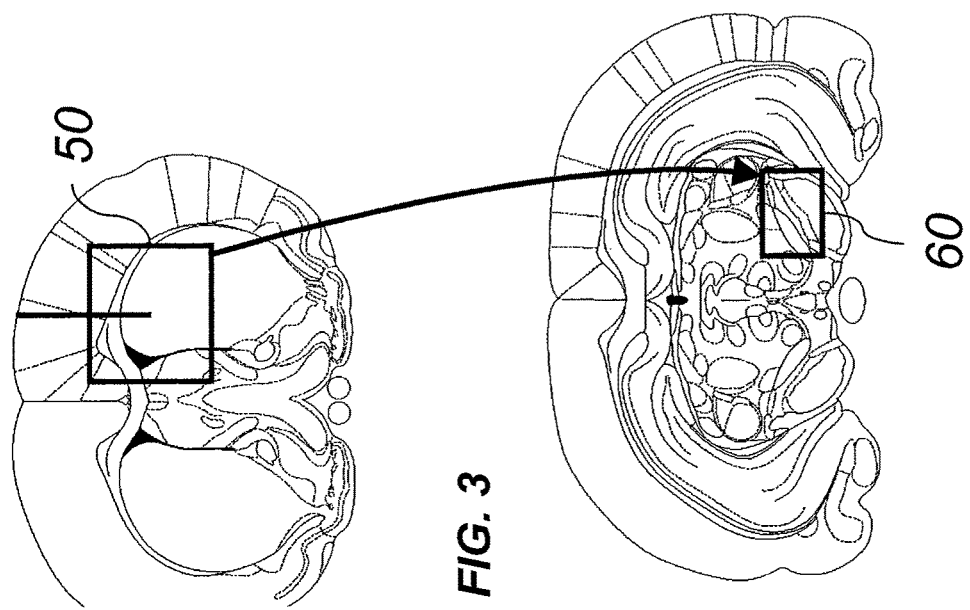
FIG. 3 depicts the axonal transport of AAV in the nigrostriatal circuit, following a high titer injection of AAV into the striatum (50) of the mouse brain. Axonal transport of AAV occurs from the injection site (represented by a vertical line) to the substantia nigra (60).

++++ high level of pathology in virtually all cells
+++ pathology in many cells, correction is observed in some cells
++ pathology in some cells, correction is observed in many cells
+ little or no pathology is in most cells, virtually every cell is corrected Thus, in accordance with the present invention, a single injection of high titer AAV2 vector is sufficient to transfer the ASM gene to structures that innervate the ASMKO affected hippocampus. The number of structures positive for AAV2 vector was greater than that demonstrated by a recent study in the normal rat hippocampus, which showed axonal transport only in the entorhinodentate circuit (Kaspar et al. (2002) Mol. Ther., 5:50-56). The results described herein demonstrate that axonal transport can occur in projection neurons inflicted with storage pathology, and that this mode of transport results in the clearance of storage pathology in proximal structures and multiple regions distal to the injection site. We also demonstrate that axonal transport is not limited to only those circuits associated with the hippocampus. Retrograde axonal transport occurred in the nigrostriatal (FIG. 3) and in the medullocerebellar (FIG. 4) circuits. This demonstrates that axonal transport of AAV2 in diseased-compromised neurons is a general property of the viral vector.

Figure 5:
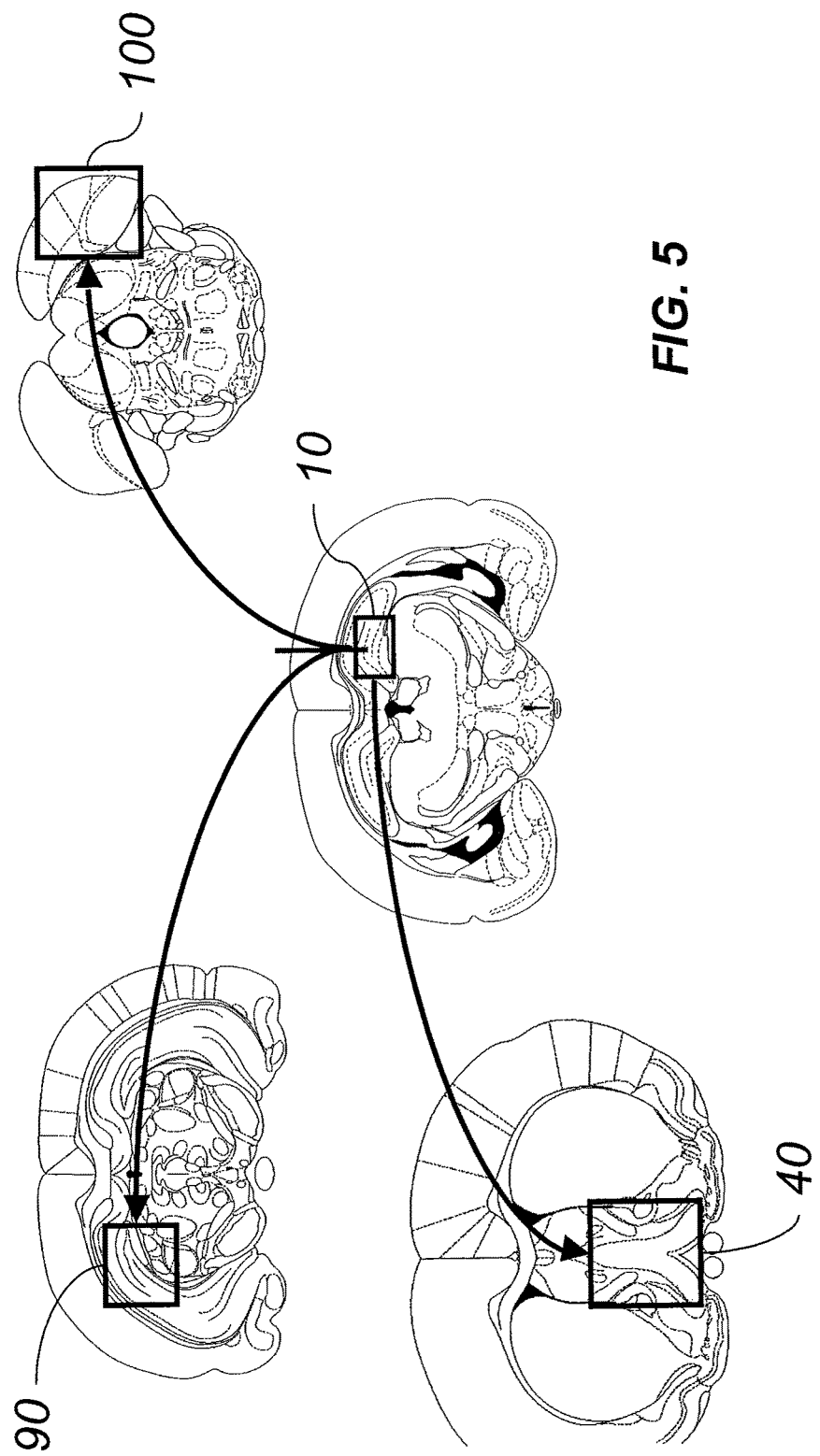
FIG. 5 depicts axonal transport of AAV in the intrahippocampal, nigrostriatal, and entorhinodentate circuits following high-titer injection of AAV7-ASM in the ipsilateral hippocampus (10). Transduced cells were detected, as determined by in situ hybridization, along the entire rostral-caudal axis of the contralateral hippocampus (90), medial septum (40), and entorhinal cortex (100) after AAV7-ASM injection of the ipsilateral hippocampus (represented by a vertical line).
Figure 7C:
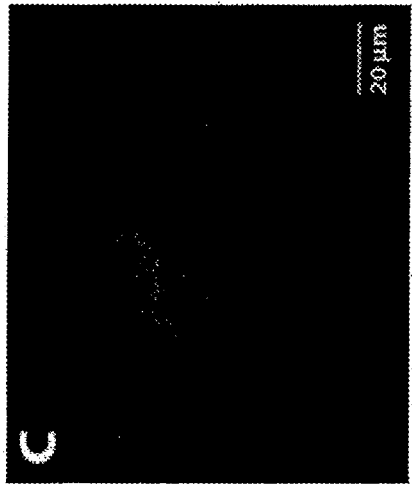
FIGS. 7A through 7E demonstrate hASM transport to the spinal cord from the deep cerebellar nuclei. This effect was observed in mice treated with AAV2/2-ASM, AAV2/5-ASM, AAV2/7-ASM & AAV2/8-ASM (A) hASM 10× magnification; (B) hASM 40× magnification; (C) confocal hASM; (D) confocal ChAT; and (E) confocal hASM & ChAT.
Figure 7D:
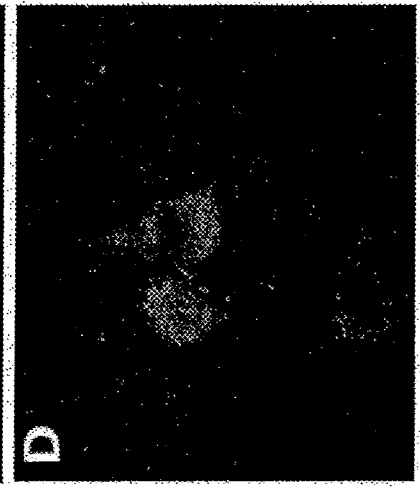
Figure 7E:
Figure 7A:
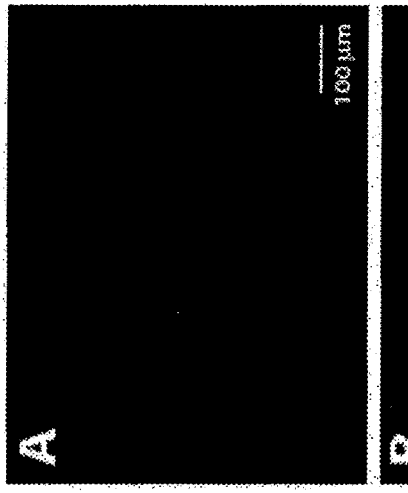
Figure 7B:

A similar study was performed with AAV1-ASM at the concentrations of $1\text{-}4\times10^{13}$ gp/ml and AAV7-ASM at the concentration of $8.4\times10^{12}$ gp/ml. While AAV1 did not exhibit detectable retrograde axonal transport, AAV7 did undergo retrograde axonal transport, similar to AAV2, and produced correction of LSD pathology in distal regions (see FIG. 5).

Injection of AAV into the Cerebellum

ASMKO mice were anesthetized with isoflurane and mounted on a stereotaxic frame. Bregma was located as a reference point to determine the drilling location for injection into the deep cerebellar nuclei region of the cerebellum. Once located, an incision was made to expose the underlying skull, and a single drill hole was made into the skull without piercing the brain surface. A Hamilton syringe was lowered into the brain via the hole and AAV2-CMV-ASM was injected into the deep cerebellar nuclei at a rate of 0.5 microliters per second. Three microliters were injected for a total dose of $1\times10^{10}$ genome particles. Mice were sacrificed 7 weeks post injection. The brains and spinal cords were evaluated for ASM mRNA expression, ASM protein expression, filipin staining, and calbindin staining.

Filipin is an autofluorescent molecule that binds to cholesterol complexes. Untreated ASMKO mice have high levels of filipin staining due to abundant cholesterol complexes, which accumulate as a result of their disease. In contrast, normal mouse brains do not exhibit filipin staining.

Calbindin is a marker of Purkinje cells, which are found in the cerebellum and are involved in coordinated movements. In the ASMKO mouse, Purkinje cells die off in these mice as they age, resulting in decreased coordinated movement behavior. This loss of Purkinje cells and the correlative loss of coordinated movement behavior are not observed in normal mice.

Following AAV2 injection into the deep cerebellar nucleus, the cerebellum was positive for ASM mRNA, ASM protein, and calbindin staining. These results demonstrate that ability of AAV2 to transduce the cerebellum following injection into the deep cerebellar nuclei. Moreover, the cerebellar transduction and resulting ASM expression prevented Purkinje cell death as evidenced by the presence of calbindin staining in the treated mice. In AAV-ASM treated mice, expression of hASM protein was also observed throughout the brainstem, thalamus, and mescencephalon. hASM protein expression in these regions overlapped with regional clearance of filipin/cholesterol staining. Overall, in the cerebellum there was a positive relationship between ASM protein levels, filipin clearance, and Purkinje cell survival.

ASM mRNA and ASM protein were also detected outside the cerebellum. Specifically, the spinal cord was positive for ASM mRNA expression as evidenced by in situ hybridization. The spinal cord was also positive for ASM protein as evidenced by ASM-specific immunofluorescence. These results indicate that the spinal cord was transduced following a distal injection of the AAV vector into the deep cerebellar nuclei. This pattern of transduction was consistent with the topographical organization of the projection neurons that innervate the deep cerebellar nuclei region. These results indicate that the AAV2 vector was taken up by distal spinal cord cells and expressed.

Treatment of Alzheimer's Disease

Alzheimer's disease (AD) is a neurodegenerative disorder characterized by the accumulation of amyloid β-peptide (Aβ) due to decreased Aβ catabolism. As Aβ accumulates, it aggregates into extracellular plaques, causing impairment of synaptic function and loss of neurons. The pathology leads to dementia, loss of coordination, and death.

Neprilysin is a 97 kD membrane-bound zinc metalloendopeptidase that is the rate-limiting enzyme in the normal degradation of Aβ. Introduction of neprilysin may decelerate the progression of the disease by removing Aβ pools before aggregation. Indeed, neprilysin was shown to degrade oligomeric forms of Aβ thereby removing existing plaques in an animal model of AD (Kanemitsu et al. (2003) Neurosci. Lett., 350:113-116). Neprilysin knockout mice exhibit high levels of Aβ (Iwata et al. (2001) J. Neurosci., 24:991-998.). Neprilysin inhibitors, such as thiorphan and phosphoramidon, increase Aβ levels in mouse brain (Iwata et al. (2000) Nat. Med., 6:143-150). Additionally, decreased neprilysin mRNA levels were found in areas of high amyloid plaque burden in human brains, further demonstrating the link between neprilysin and AD (Yasojima et al. (2001) Neurosci. Lett., 297:97-100).

The areas of brain most affected by AD are the hippocampus, cortex, cerebellum, striatum and thalamus (see, e.g., Iwata et al. (2001) supra; Yasojima et al. (2001) supra).

These are the same areas of the brain that show efficient retrograde axonal transport with AAV.

Accordingly, AAV can used to deliver therapeutic transgenes to regions of high plaque burden by direct injection and subsequent translocation of virus through brain circuits to our target sites. Viral vector-mediated gene transfer of neprilysin was effective in treating mouse models of AD (Marr et al. (2003) J. Neurosci., 23:1992-1996; Marr et al. (2004) J. Mol. Neurosci., 22:5-11; Iwata et al. (2004) J. Neurosci., 24:991-998). A recent report showed that AAV5-neprilysin removed Aβ from the pre-synaptic terminals of the hippocampus in neprilysin-deficient mice, decelerating plaque formation at the synapses (Iwata et al. (2004) supra). In this report, neprilsyin was found in the contralateral hippocampus but whether this is attributable to retrograde transport of virus or anterograde transport of expressed protein remains unknown.

Correction of Cholesterol Storage Pathology

The following experiment, evaluated the relative ability of recombinant AAV2/1, AAV2/2, AAV2/5, AAV2/7 and AAV2/8 serotype vectors encoding human ASM (hASM) to express hASM protein, correct cholesterol storage pathology, undergo transport, rescue Purkinje cells, and initiate functional recovery in the ASMKO mouse after unilateral injection within the deep cerebellar nuclei. An additional group of ASMKO mice received bilateral injections into the DCN in order to assess whether increased transgene protein spread/expression would improve behavioral functional recovery.

Sixty-six male homozygous (−/−) acid sphingomyelinase knockout (ASMKO) mice and sixteen male wild type littermate controls were bred from heterozygote matings (+/−). Mice were genotyped by PCR following the procedure described in Gal et al. (1975) N Engl J Med: 293:632-636. Mice from the original colony were backcrossed onto the C57/Bl6 strain. Animals were housed under 12:12 hour light:dark cycle and provided with food and water ad libitum. All procedures were performed under a protocol approved by the Institutional Animal Care and Use Committee.

After being anesthetized with isoflurane, mice (~7 weeks of age) were unilaterally injected into the deep cerebellar nuclei (DCN) (A-P: −5.75 from bregma, M-L: −1.8 from bregma, D-V: −2.6 from dura, incisor bar: 0.0) with one of the following AAV serotype vectors (n=8/vector): AAV1-CMV-βgal, AAV1-CMV-ASM, AAV2-CMV-ASM, AAV5-CMV-ASM, AAV7-CMV-ASM, and AAV8-CMV-ASM. Vectors were delivered with a 10 μl Hamilton syringe mounted on a syringe pump at a rate of 0.5 μl/minute for a total of $1.86 \times 10^{10}$ genome particles per brain. The final injection volume for each vector was 4 μl. One hour before and twenty-four hours after surgery mice were given ketoprofen (5 mg/kg; SC) for analgesia. Mice were killed 7 weeks post-injection (14 weeks of age). At the time of sacrifice mice were overdosed with euthasol (150 mg/kg; IP) and rapidly decapitated (n=5/group) or transcardially perfused (n=3/group). Brains from decapitated mice were rapidly removed, snap frozen in liquid nitrogen, dissected into 3 sections (right cerebral hemisphere, left cerebral hemisphere, & cerebellum) homogenized, and analyzed for hASM by ELISA. Brains and spinal cords from perfused mice were processed for human ASM protein expression, cholesterol accumulation as detected by filipin staining, and Purkinje cell survival with calbindin staining on 50 μm vibratone sections.

Using a similar protocol, ASMKO mice (~7 weeks of age) were injected bilaterally with AAV2/1-βgal (n=8), AAV2/1-ASM (n=5), and AAV2/2-ASM (n=5) and sacrificed at 20 weeks of age after undergoing rotarod testing. Brains were snap frozen in liquid nitrogen, bisected at midline and then divided into five sections (S1, S2, S3, S4, and S5) using a mouse brain matrix (ASI Instruments, Inc, MI.) Sections 1-4 were approximately 2 mm apart with S1 being the most rostral and S4 the most caudal. Section 5 contained the cerebellum only. The right hemisphere was used to quantify brain spingomyelin levels and the left hASM levels.

The full-length human ASM cDNA under the control of the human cytomegalovirus immediate-early (CMV) promoter, with an SV40 polyadenylation sequence, and a hybrid intron, was cloned into a plasmid containing ITRs from AAV serotype 2 (AAV2 ITR). Jin et al. (2002) J Clin Invest. 109:1183-1191. Hybrid vectors were produced by triple transfection using a series of helper plasmids containing serotype specific capsid coding domains in addition to the AAV type 2 replication genes. This strategy allows the packaging of AAV2 ITR vectors into each serotype-specific virion Rabinowitz, et al. (2002) J Virol. 76:791-801. With this approach the hASM recombinant genome was used to generate a series of rAAV-hASM vectors of various serotypes including AAV2/1, AAV2/2, AAV2/5, AAV2/7 and AAV2/8. Recombinant AAV vectors were purified by ion-exchange chromatography (Serotypes 2/1, 2/2 and 2/5). O'Riordan, et al. (2000) J Gene Med 2: 444-54 or CsCl centrifugation (serotypes 2/8 and 2/7) Rabinowitz et al. (2002) J. Urrol. 76:791-801. The final titer of AAV-ASM virion particles (DNAse-resistant particles), was determined by TaqMan PCR of the CMV sequence. Clark et al. (1999) Hum. Gene Therapy 10:1031-1039.

Human ASM antibodies are human specific and do not cross react with mouse ASM. Coster (Corning, NY) 9018 plates coated (100 μl/well) with monoclonal recombinant human ASM (rhASM) antibody (2 μg/ml) diluted in 50 mM sodium carbonate buffer (pH 9.6) were incubated overnight @ 2-8° C. Excess coating antibody was removed and blocking diluent (KPL, Inc., MD) was added for 1 h @ 37° C. Plates were washed with a microplate washer (Molecular Devices, CA) for two cycles. Standards, controls and samples diluted in standard dilution buffer (PBS, 0.05% Tween, 1% HP-BSA) were pipetted in duplicate and allowed to incubate for 1 h @ 37° C. Plates were washed as described above. One hundred microliters of biotinylated recombinant human ASM (rhASM) antibody (diluted 1:20K in standard dilution buffer) was added to each well, allowed to incubate for 1 h @ 37° C., and then removed with a microplate washer. Streptavidin-HRP (Pierce Biotechnology, Inc., IL) diluted 1:10K was then added (100 μl/well) and allowed to incubate for 30 min at room temperature. Plates were washed as described above and then incubated with Sure-Blue TMB (KPL, Inc., MD) for 15 minutes @ 36-38° C. The reaction was stopped with stop solution (KPL, Inc., MD) and absorbance values were then read at 450 nm with a Spectra Max 340 plate reader (Molecular Devices, CA). Data analysis was completed using Softmax Pro 4.3 software (Molecular Devices, CA).

The protein concentration for each sample was determined with a BCA protein assay kit (Pierce Biotechnology, Inc., IL) using bovine serum albumin as standard.

Mice were transcardially perfused with fixative containing 2% paraformaldehyde, 0.03% glutaraldehyde, 0.002% $CaCl_2$ in 0.1 M sodium acetate buffer at pH 6.5, followed by perfusion with the same fixative at pH 8.5. Mouse brains and spinal cords were dissected, and post-fixed overnight at 4° C. in pH 8.5 fixative without glutaraldehyde. The tissues were washed in 0.1 M potassium phosphate buffer, pH 7.4, embedded in 3.5% agar and cut into 50 µm sagittal sections with a vibratome.

Brains and spinal cords were vibratome-sectioned sagittally at 50 µm intervals. Sections were processed for immunofluorescence with primary antibodies against human ASM (1:200). Sections were incubated in 10% donkey serum, 0.3% Triton X-100 in PBS for 1 hour, followed by incubation with biotinylated mouse anti-human ASM in 2% donkey serum, 0.2% Triton X-100 in PBS for 72 hours. After washing, the signal was amplified using a Tyramide Signal Amplification kit (PerkinElmer, Boston MA). Human ASM protein was visualized with a Nikon fluorescent microscope, and images were captured with a SPOT camera and Adobe Photoshop software.

Filipin Complex (Sigma, St. Louis, MO) was first diluted in 100% methanol for a stock concentration of 1 mg/ml. Stock solution is stable for 4 weeks at −20° C. After washing with PBS, the sections were incubated in the dark for three hours in a freshly made 10 µg/ml filipin solution in PBS. Sections were then washed three times with PBS. Cholesterol deposits were visualized under an ultraviolet filter on a fluorescence microscope.

Brains were processed for immunofluorescence using primary antibodies directed against the calcium binding protein, calbindin. Sections were washed with potassium phosphate buffer (KPB) and then rinsed with potassium phosphate buffered saline (KPBS). Sections were then blocked in 5% donkey serum, 0.25% Triton X-100 in KPBS for up to 3 hours and then incubated in 5% donkey serum, 0.2% Triton X-100 and mouse anti-calbindin (1:2500, Sigma, St. Louis, MO) in KPBS. After 72 hours at 4° C. sections were rinsed with KPBS with 0.1% Triton X-100 three times. Secondary antibody, donkey-anti mouse CY3 (1:333, Jackson Immunoresearch Laboratories, West Grove, PA) was added in KPBS+0.1% Triton X-100 for 90 minutes at room temperature. Sections were washed with KPB and then mounted onto gel-coated slides. Calbindin-positive cells were visualized under epifluorescence. In order to quantify Purkinje cells of the cerebellum, four full-faced, medial cerebellar sections were selected from each animal. Calbindin-immunopositive Purkinje cells were viewed under a fluorescent microscope and cell bodies were counted at a magnification of 20×. Each lobe was counted separately. Two separate focal planes were counted per lobe. Only cells in focus were counted to insure that no cell was counted twice.

Fifty (50) µm vibratome sections were first processed for immunofluorescence with antibodies directed against human ASM, as described above. The sections were then washed in PBS and stained for choline acetyltransferase (ChAT; rabbit polyclonal, 1:500, Chemicon International, Temecula, CA) with the protocol outlined above for calbindin. Rather than using a CY3 secondary antibody, however, donkey-anti-rabbit FITC (1:200, Jackson Immunoresearch Laboratories, West Grove, PA) was used. The staining was first visualized under epifluorescence and later images were acquired with a confocal microscope.

Filipin staining was quantified as follows. Exposure-matched images were captured using a Nikon E600 wide field upright epifluorescence microscope equipped with a SPOT digital camera. The AAV2/1-ß-gal group was imaged first, and that exposure was used to acquire all additional images. Each image analyzed represents a medial sagittal plane through the length of each half-brain. Morphometric analysis was performed with Metamorph software (Universal Imaging Corporation). The AAV2/1-ß-gal images were thresholded; once established, the same threshold was used in all images. The following regions were manually selected by the user and analyzed separately: cerebellum, pons, medulla, midbrain, cerebral cortex, hippocampus, thalamus, hypothalamus and striatum. Integrated intensity was measured in each region, and all measurements (n=3/group) from a given group of animals were used to generate averages. The reduction in cholesterol in the treated animals was then calculated as the percent decrease of the integrated intensity compared to the knockout ß-gal injected mice.

Positive hASM immunostaining was observed throughout the cerebellum (FIG. 6, Table 3), pons, medulla and spinal cord (FIG. 7) following unilateral injection of AAV-ASM within the deep cerebellar nuclei.

TABLE 3

Areas with positive hASM staining as function of AAV serotype.

| Structure | AAV1 | AAV2 | AAV5 | AAV7 | AAV8 |
|---|---|---|---|---|---|
| deep cerebellar nuclei | ++++ | ++ | +++ | +++ | ++++ |
| cerebellar lobules | ++++ | ++ | +++ | +++ | ++++ |
| pons | ++ | ++ | ++ | ++ | + |
| medulla | + | ++ | ++ | +++ | + |
| spinal cord |  | +++ | +++ | ++ | + |
| thalamus | * | * | * | * | * |
| hypothalamus | * | * | * | * | * |
| hippocampus | * | * | * | * | * |
| striatum | * | * | * | * | * |
| cerebral cortex | * | * | * | * | * |

Figure 8:
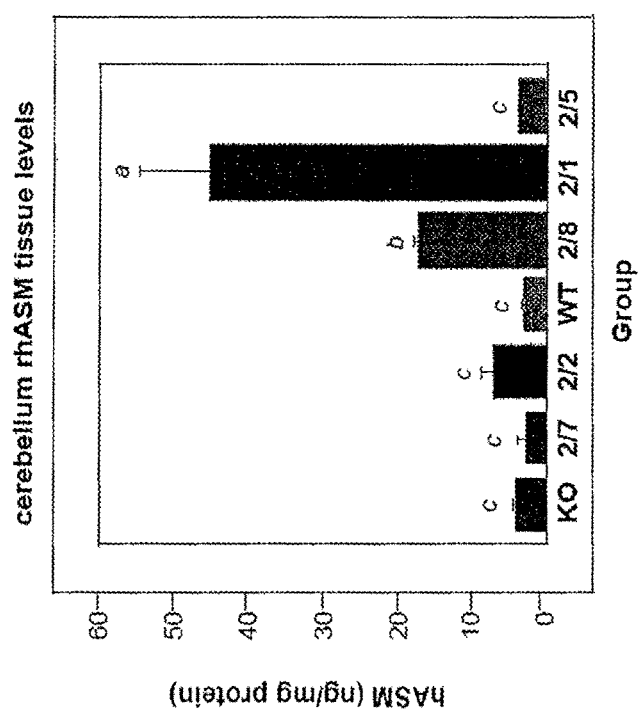
FIG. 8 shows cerebellar tissue homogenate levels following injection of different AAV serotype vectors (2/1, 2/2, 2/5, 2/7 and 2/8) encoding for human ASM into the deep cerebellar nuclei (n=5/group). Groups not connected by the same letter are significantly (p<0.0001) different.

* indicates positive hASM was below limit of detection, but correction of cholesterol pathology still occurred Within the cerebellum mice treated with AAV2/1-ASM and had the most widespread (i.e., spread between lobules within the same sagittal section) level of hASM expression, whereas mice treated with AAV2/2-ASM had the most restricted level of Human ASM protein expression. Human ASM protein expression in mice treated with AAV2/5-ASM, AAV2/7-ASM, and AAV2/8-ASM was intermediate between these two groups. Medial-lateral spread between sagittal sections was maximal in mice treated with serotypes 1 & 8 and minimal is mice injected with serotype 2. Serotypes 5 & 7 initiated medial-lateral spread patterns intermediate between serotypes 1 and 2. Each layer of the cerebellum (i.e., molecular, Purkinje and granular) was transduced by each AAV serotype; however, an increased affinity for the molecular layer was apparent for all serotypes. Purkinje cell transduction was maximal in mice treated with serotypes 1 and 5. Mice injected with serotype 7 had the fewest number of transduced Purkinje cells. Mice treated with serotype 8 also had few transduced Purkinje cells, but had less ASM expression within the granular layer when compared to serotypes 1, 2, 5 & 7. Purkinje cells transduced with ASM appeared to have a healthy cytostructure. Quantitative analysis of AAV mediated hASM protein expression by ELISA in cerebellar tissue homogenates supports our immunohistochemical findings. Mice injected with serotypes 1 and 8 demonstrated significantly (p<0.0001) higher cerebellum hASM protein levels when compared to all other mice (FIG. 8). Cerebellar hASM levels from mice injected with serotypes 2, 5, & 7 were not above WT levels (i.e. background). As expected Human ASM was not detected in wild type mice—the hASM antibody used in the ELISA are human specific.

An absence of functional ASM protein results in lysosomal accumulation of sphingomyelin, and subsequent secondary metabolic defects such as abnormal cholesterol trafficking. Sarna et al. Eur. J. Neurosci. 13:1873-1880 and Leventhal et al. (2001) J. Biol. Chem. 276:44976-4498. Free cholesterol buildup in the ASMKO mouse brain is visualized using filipin, an autofluorescent molecule isolated from streptomyces filipinensis. Wild-type mouse brains do not stain positively for filipin. In all AAV treated mice (with exception to AAV2/1-βgal) clearance of filipin staining (Table 4) overlapped with areas that were positive for hASM immunostaining indicating that each serotype vector is capable of generating a functional transgene product.

TABLE 4

Percent Reduction in Filipin (i.e., cholesterol) clearance as compared to ASMKO mice treated with AAV- βgal in selected brain regions following intracerebellar injection of different AAV serotypes (n = 3/serotype; 2/1, 2/2, 2/5, 2/7, and 2/8) encoding for human ASM into the deep cerebellar nuclei of ASMKO mice.

|  | 2/1 | 2/2 | 2/5 | 2/7 | 2/8 |
|---|---|---|---|---|---|
| Cerebellum | 96.54 ± 2.14 | 93.85 ± 1.257 | 86.75 ± 9.58 | 96.47 ± 1.93 | 99.12 ± .66 |
| Midbrain | 96.72 ± 1.73 | 53.08 ± 22.89 | 65.88 ± 24.53 | 73.39 ± 22.39 | 91.10 ± .105 |
| Pons | 91.31 ± 5.80 | 50.07 ± 21.26 | 70.96 ± 25.60 | 93.15 ± 31.20 | 96.72 ± 1.20 |
| Medulla | 93.29 ± 6.22 | 88.46 ± 3.04 | 81.55 ± 17.31 | 80.73 ± 14.99 | 97.40 ± 1.60 |
| Thalamus | 48.88 ± 25.25 | 41.21 ± 27.35 | 34.86 ± 16.67 | 48.44 ± 28.65 | 77.03 ± 12.08 |
| Hypothalamus | 82.81 ± 10.14 | 86.96 ± 12.93 | 88.46 ± 5.90 | 82.95 ± 11.46 | 99.68 ± .31 |
| Cortex | 27.60 ± 24.75 | 73.62 ± 14.9 | 55.65 ± 28.89 | 76.97 ± 14.27 | 98.30 ± .34 |

Orlando, FL). Calbindin is a widely accepted Purkinje cell marker. Positive calbindin staining in AAV-ASM treated mice would suggest that AAV mediated expression of hASM is therapeutic. Overall our results indicate that AAV mediated hASM expression in the cerebellum prevents Purkinje cell death in the ASMKO mouse (Table 5, FIG. 9). As expected Purkinje cell survival did not occur in lobules I-III; mice were injected at 7 weeks of age and by 8 weeks the majority of these cells have already died off. Purkinje cell survival in lobules IV/V was maximal in mice treated with serotype 1. In lobule VI no significant Purkinje cell survival was observed in AAV treated mice. In lobule VII only mice treated with serotype 5 showed significant Purkinje cell survival. In lobule VIII again mice treated with serotype 5 as well as serotype 2 showed significant Purkinje cell survival. In lobules IX and X there were no significant differences between WT and KO mice (or between AAV treated mice) in Purkinje cell counts. This was expected, because at 14 weeks of age (i.e., age at sacrifice) Purkinje cells in these lobules are still viable in ASMKO mice. Across all lobules Purkinje cell survival was maximal in mice treated with serotypes 1, 2, & 5 and minimal in mice treated with serotypes 7 & 8. Purkinje cell survival (based on calbindin staining) in the anterior cerebellar lobules was greatest in mice that were injected with serotype 1.

Purkinje cell counts in cerebellar lobules I-X in WT and ASMKO mice following intracerebellar injection of different AAV serotypes (n=3/serotype; 2/1, 2/2, 2/5, 2/7, and 2/8) encoding for human ASM into the deep cerebellar nuclei of ASMKO mice. Numbers appearing bold italic are significantly different from KO mice (i.e., mice treated with AAV2/1-βgal) p≤0.01

|  | 2/1 | 2/2 | 2/5 | 2/7 | 2/8 | KO | WT |
|---|---|---|---|---|---|---|---|
| I/II | 7.42 ± 9.80 | 4.5 ± 10.58 | 9.40 ± 11.59 | 12.33 ± 10.58 | 1 ± 9.16 | 5.8 ± 11.59 | *113 ± 10.58* |
| III | 12.42 ± 10.32 | 11.33 ± 11.14 | 26.80 ± 12.21 | 15.33 ± 11.14 | 9.8 ± 12.21 | 2 ± 9.65 | *147.50 ± 11.14* |
| IV/V | *60.57 ± 17.28* | 36.5 ± 18.67 | 27.80 ± 20.45 | 29.66 ± 18.67 | 6.8 ± 20.45 | 8 ± 16.16 | *220.66 ± 18.67* |
| VI | 61.14 ± 11.21 | 27.5 ± 12.11 | 72.20 ± 13.26 | 31.16 ± 12.11 | 3.8 ± 13.26 | 68.5 ± 10.48 | *121.16 ± 12.11* |
| VII | 17.42 ± 4.15 | *37.66 ± 4.49* | *40.60 ± 4.49* | 5.33 ± 4.49 | .2 ± 4.95 | 17.37 ± 3.88 | *7.16 ± 4.49* |
| VIII | 44.14 ± 10.75 | 48.66 ± 11.62 | *82.80 ± 12.73* | 11.33 ± 11.62 | 18.40 ± 12.73 | 35.12 ± 10.06 | *103.33 ± 11.62* |
| IX | 126.28 ± 19.17 | 102.66 ± 20.71 | 136.40 ± 22.68 | 60.16 ± 20.71 | 84.40 ± 22.68 | 108.0 ± 17.93 | 144 ± 20.71 |
| X | 89.85 ± 12.54 | 76.83 ± 13.55 | 93.80 ± 14.84 | 48.16 ± 13.55 | 64.80 ± 14.84 | 87 ± 11.73 | 86.66 ± 13.55 |

As previously demonstrated by (Passini et al. (2003) in "Society for Neuroscience" New Orleans, LA), filipin clearance also occurred in areas anatomically connected with the injection site, but that did not stain positively for hASM. MetaMorph analysis indicated that a reduction in filipin staining occurred throughout the entire rostral caudal axis. In the cerebellum and brainstem filipin was maximally reduced in mice treated with AAV2/1-ASM and AAV2/8-ASM, whereas in the diencephalon and cerebral cortex mice injected with AAV2/8-ASM had the best overall level of filipin clearance (Table 4). Nevertheless, these results indicate that the level of hASM required to correct cholesterol storage pathology is the ASMKO mouse CNS is minimal (i.e., below the hASM immunoflourescence limit of detection).

Table 5

Histological studies indicate that the ASMKO mouse cerebellum undergoes rapid deterioration. More specifically, Purkinje cells progressively die off between 8 and 20 weeks of age (Sarna et al. (2001) Eur. J. Neurosci. 13:1813-1880 and Stewart et al. (2002) in "Society for Neuroscience"

Figure 10B:
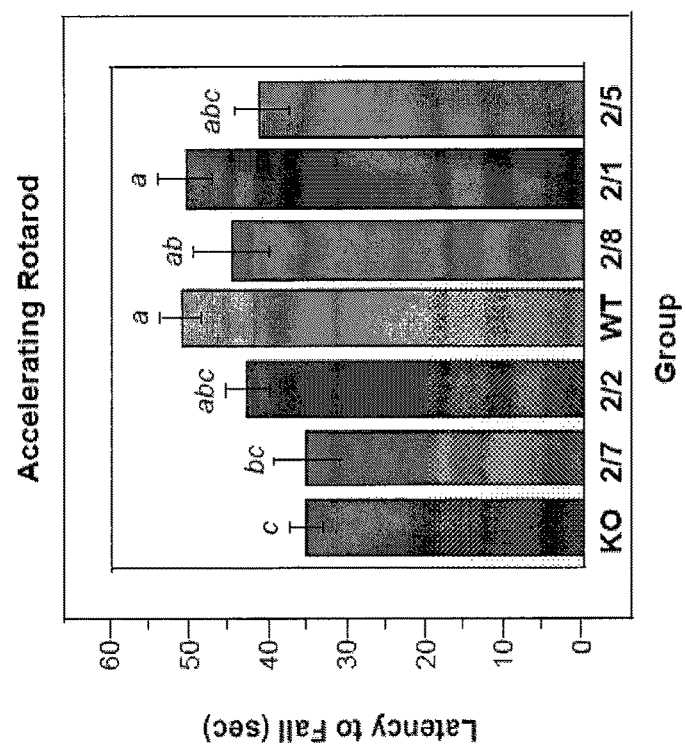
Figures 11A, 11B:
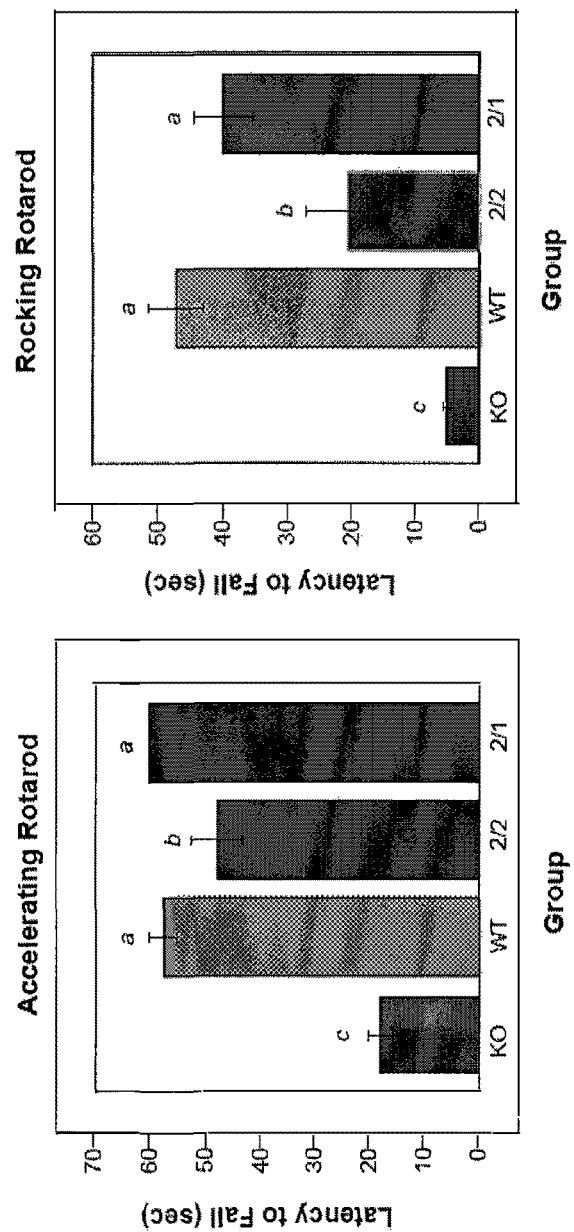
FIGS. 11A and 11B show Rotarod performance in ASMKO (n=8), WT (n=8), and bilaterally AAV-ASM (n=5/group) treated mice (at 20 weeks of age). For both accelerating and rocking test, AAV-ASM treated mice performed significantly (p<0.001) better than ASMKO AAV2/1-βgal treated mice. Performance of mice injected with AAV2/1-ASM were indistinguishable from wild type mice in both the accelerating and rocking tests.

On the accelerating rotarod test mice unilaterally injected with AAV2/1-ASM and AAV2/8-ASM demonstrated a significantly (p<0.0009) longer latency to fall than ASMKO mice injected with AAV2/1-βgal (FIG. 10A). Mice injected with serotype AA2/1-ASM were not significantly different from wild type mice. Mice injected with AAV2/2-ASM and AAV2/5-ASM showed a trend for a longer latency to fall than ASMKO mice injected with AAV2/1-βgal; whereas, mice injected with AAV2/7-ASM did not. For the rocking rotarod test, only mice injected with AA2/1-ASM demonstrated a significantly (p<0.0001) longer latency to fall than mice injected with AA2/1-βgal. In this case wild type mice performed significantly better than mice injected with AA2/1-ASM (FIG. 10B). ASMKO mice that received bilateral injection of either AAV2/1-ASM or AAV2/2-ASM performed significantly (p<0.001) better than ASMKO AAV2/1-βgal treated mice for both accelerating and rocking tests (FIGS. 11A and 11B). AAV2/1-ASM bilaterally injected mice performed comparably to wild type mice for both tests.

One way to determine if AAV generated hASM is functionally active within the ASMKO CNS is to assess its influence on cholesterol storage pathology—a secondary metabolic defect of NPA disease. In all AAV treated mice (with exception to AAV2/1-βgal) correction of cholesterol storage pathology overlapped with areas that were positive for hASM immunostaining indicating that each serotype vector is capable of generating a functional transgene product. As previously demonstrated, correction of abnormal cholesterol metabolism correction also occurred in areas anatomically connected with the injection site, but also in regions that did not stain positively for hASM, suggesting that the level hASM required for correction of cholesterol storage pathology is minimal. Consistent with our hASM histochemical and biochemical results mice treated with serotypes 1 and 8 demonstrated a marked reduction in cholesterol storage pathology. Mice treated with serotypes 2, 5, & 7 also showed a reduction in cholesterol storage pathology, but not to the same extent as mice treated with serotypes 1 & 8.

Figure 12:
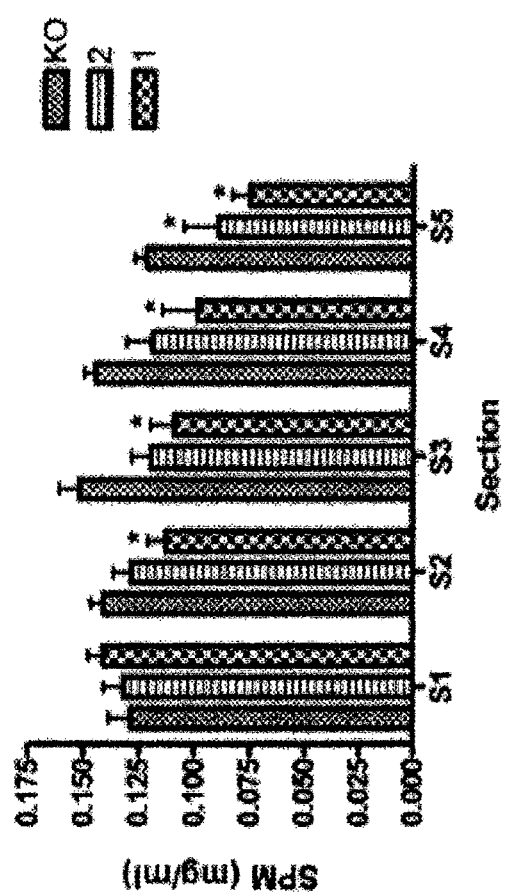
FIG. 12 shows brain sphingomyelin levels (at 20 weeks of age) in ASMKO mice bilaterally injected with AAV1-βgal or with AAV serotypes 1 and 2 encoding for hASM. Brains were divided into 5 rostrocaudal sections (S1=most rostral and S5=most caudal. An asterisk indicates that the data point is significantly different from ASMKO mice (p<0.01).
Figure 13A:
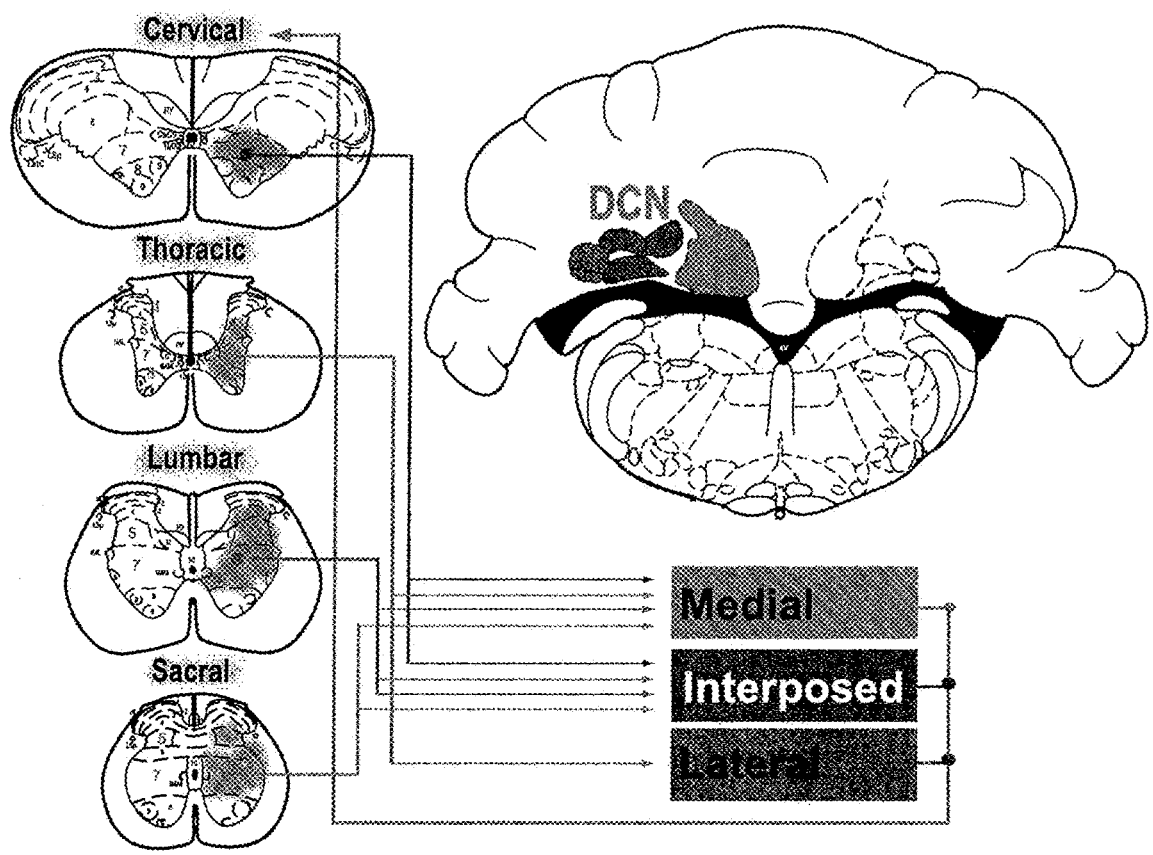
FIG. 13A illustrates the connections between the deep cerebellar nuclei regions (medial, interposed, and lateral) and the spinal cord regions (cervical, thoracic, lumbar, and sacral).

While cholesterol storage pathology changes are illustrative, a more direct measurement of hASM enzyme activity is through the analysis of sphingomyelin levels, which is the primary substrate accumulated in the tissues of mammals with Niemann-Pick disease. Brain tissue from mice that received bilateral injections of AAV serotype 1 and 2 were assayed for sphingomyelin (SPM) levels (the tissue homogenization procedure for detection of SPM is not compatible with the detection of hASM.) A significant reduction ($p<0.01$) in SPM tissue content in the cerebellum was observed in mice treated with both serotypes 1 and 2 (FIG. 12). SPM tissue content levels were also significantly reduced in sections 2, 3, and 4 (each section being 2 mm apart from the next) in mice injected with serotype 1 but not in mice injected with serotype 2.

ASMKO mice that received bilateral intracerebellar injections of AAV serotypes 1 and 2 encoding for hASM showed a significant reduction in sphingomyelin storage within the cerebellum. As observed with cholesterol storage accumulation, a significant reduction in sphingomyelin storage also occurred in regions outside the cerebellum in ASMKO mice bilaterally treated with AAV1.

Overall, these results indicate that AAV1 is preferred over serotypes 2, 5, 7, and 8 in its relative ability to initiate enzyme expression, correct storage pathology in the brain, prevent neurodegeneration (by, for example, preventing Purkinje cell death), and improve motor functional outcome. In addition, the DCN can be exploited as an injection site to maximize enzyme expression throughout the CNS.

To evaluate the distribution of transgene expression following injection of AAV vectors into the DCN, G93A SOD1 ($SOD1^{G93A}$ mutant mouse, referred to here at the SOD1 mouse) were injected recombinant AAV vectors encoding for green fluorescent protein (GFP). One group of mice was injected with AAV serotype 1 encoding for green fluorescent protein (AAV1-GFP) while another group was injected with AAV serotype 2 encoding for green fluorescent protein (AAV2-GFP).

The mice were injected bilaterally into the DCN with the AAV recombinant vectors using methods similar to those described above. The dose was approximately 2.0 e10 gc/ml injected per site. Mice were sacrificed about 110 days after birth and their brain and spinal cord were analyzed for GFP staining.

Figure 14:
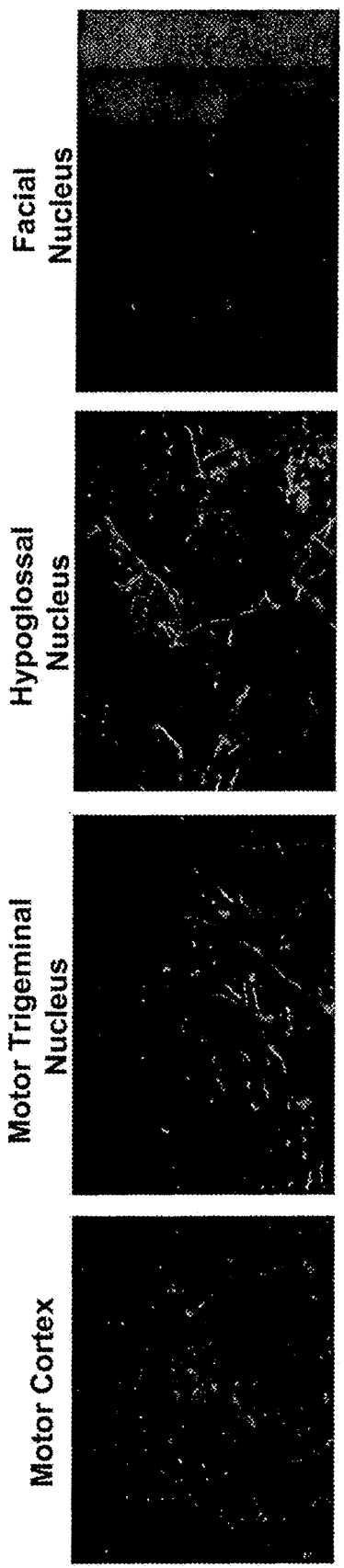
FIG. 14 illustrates green fluorescent protein distribution in the brainstem, or upper motor neurons, following DCN delivery of AAV encoding for green fluorescent protein (GFP).
Figure 15:
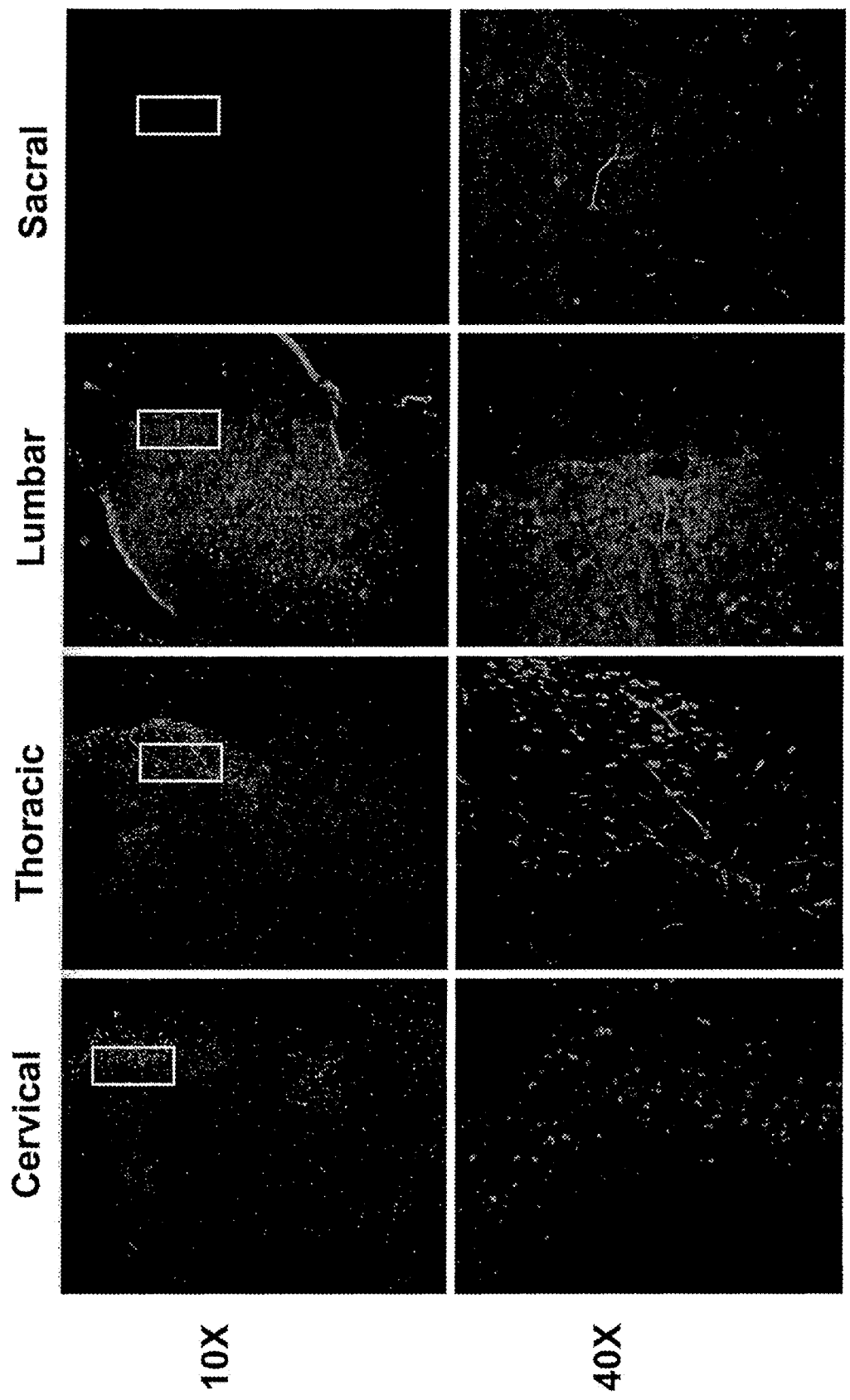
FIG. 15 illustrates green fluorescent protein distribution in the spinal cord regions following DCN delivery of AAV encoding for green fluorescent protein (GFP).
Figure 16:
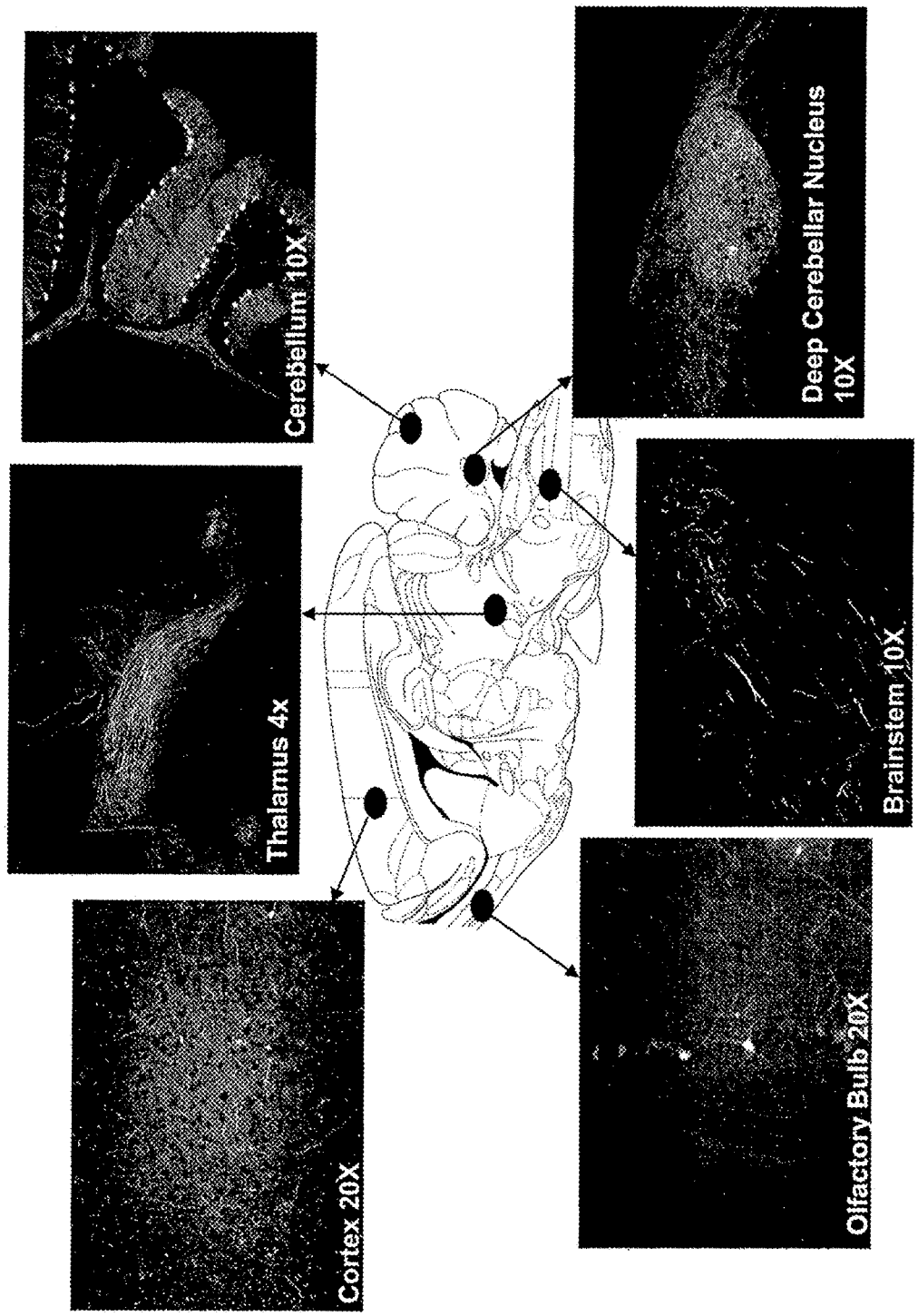
FIG. 16 shows GFP distribution within the mouse brain following bilateral delivery of a GFP expressing AAV1 vector to the deep cerebellar nuclei (DCN). In addition to the DCN, GFP positive staining was also observed in the olfactory bulbs, cerebral cortex, thalamus, brainstem, cerebellar cortex and spinal cord. All of these areas either receive projections from and/or send projections to the DCN.

Green fluorescent protein distribution was observed in the brainstem (see FIG. 14) and in the spinal cord regions (see FIG. 15) following DCN delivery of AAV encoding for green fluorescent protein (GFP). GFP staining was also observed in the DCN as well as in the olfactory bulbs, cerebral cortex, thalamus, brainstem, cerebellar cortex and spinal cord. All of these areas either receive projections from and/or send projections to the DCN (see FIG. 16).

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, and biological sequences cited in this disclosure are incorporated by reference in their entirety. To the extent the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may very depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

The invention claimed is:

1. A method of treating Alzheimer's disease in a mammal comprising: administering a composition comprising an AAV vector having an AAV serotype 1 capsid encoding for a biologically active metalloendopeptidase molecule to the deep cerebellar nuclei of the cerebellum in the disease compromised central nervous system (CM) of the mammal with Alzheimer's disease, under conditions whereby said injected AAV vectors transduce cells located at a distal site in the central nervous system and said encoded biologically active metalloendopeptidase is expressed at a therapeutic level.

2. The method of claim 1, wherein the metalloendopeptidase is selected from the group consisting of neprilysin, insulysin, and thimet oligopeptidase.

3. The method of claim 1, wherein the AAV vector is AAV 2/1.

4. The method of claim 1, wherein the distance between the administration site and the distal site is at least 2 mm.

5. The method of claim 1, wherein the concentration of the V vector in the composition is at least $5\times10^{12}$ gp/ml.

6. The method of claim 5, wherein the AAV is AAV2/1.

7. The method of claim 1, wherein the mammal is human.

8. The method of claim 1, wherein the distal site is contralateral to the administration site.

9. The method of claim 1, further comprising administration of a composition to a second site in the CNS of the mammal, wherein the composition comprises an AAV vector comprising a polynucleotide encoding a biologically active metalloendopeptidase.

* * * * *